(12) United States Patent
Cleland et al.

(10) Patent No.: US 7,163,701 B2
(45) Date of Patent: *Jan. 16, 2007

(54) CONTROLLED RELEASE MICROENCAPSULATED NGF FORMULATION

(75) Inventors: Jeffrey L. Cleland, San Carlos, CA (US); Xanthe M. Lam, San Francisco, CA (US); Eileen T. Duenas, San Jose, CA (US)

(73) Assignee: Genentech, Inc., South San Francisco, CA (US)

( * ) Notice: Subject to any disclaimer, the term of this patent is extended or adjusted under 35 U.S.C. 154(b) by 584 days.

This patent is subject to a terminal disclaimer.

(21) Appl. No.: 10/442,894

(22) Filed: May 20, 2003

(65) Prior Publication Data

US 2003/0203040 A1    Oct. 30, 2003

Related U.S. Application Data

(63) Continuation of application No. 09/095,911, filed on Jun. 11, 1998, now Pat. No. 6,663,899.

(60) Provisional application No. 60/049,541, filed on Jun. 13, 1997.

(51) Int. Cl.
    *A61K 9/64*    (2006.01)

(52) U.S. Cl. ...................... 424/491; 530/399

(58) Field of Classification Search .............. 424/491; 530/399

See application file for complete search history.

(56) References Cited

U.S. PATENT DOCUMENTS

| | | | |
|---|---|---|---|
| 3,773,919 A | 11/1973 | Boswell | |
| 4,485,045 A | 11/1984 | Regen | |
| 4,544,545 A | 10/1985 | Ryan et al. | |
| 5,013,556 A | 5/1991 | Woodle et al. | |
| 5,288,622 A | 2/1994 | Gray et al. | |
| 5,488,099 A | 1/1996 | Persson et al. | |
| 5,589,167 A | 12/1996 | Cleland et al. | |

FOREIGN PATENT DOCUMENTS

| | | |
|---|---|---|
| DE | 3218121 | 11/1983 |
| EP | 36676 | 9/1981 |
| EP | 52322 | 5/1982 |
| EP | 58481 | 8/1982 |
| EP | 88046 | 9/1983 |
| EP | 102324 | 3/1984 |
| EP | 142641 | 5/1985 |
| EP | 143949 | 6/1985 |
| EP | 172636 | 2/1986 |
| JP | 92028412 | 5/1992 |
| WO | WO 94 19020 | 9/1994 |
| WO | WO 95/33829 | 12/1995 |
| WO | WO 96 40072 | 12/1996 |
| WO | WO 97/17087 | 5/1997 |

OTHER PUBLICATIONS

Mahoney et al., "Controlled Release of Proteins to Tissue Transplants for the Treatment of Neurodegenerative Disorders", Journal of Pharmaceutical Sciences, vol. 85 (12) 1276-1281, Dec. 1996.

Angeletti et al., "Nerve Growth Factor From Mouse Submaxillary Gland: Amino Acid Sequence" *Proc. Natl. Acad. Sci. USA* 68 (10): 2417-2420 (1971).

Apfel et al., "Nerve Growth Factor Prevents Experimental Cisplatin Neuropathy" *Ann. Neurol.* 31: 76-80 (1992).

Apfel et al., "Nerve Growth Factor Prevents Toxic Neuropathy in Mice" *Annals of Neurology* 29(1):87-90 (Jan. 1991).

Berman et al., "Age-Related Changes in Regional Cerebral Blood Flow and Behavior in Sprague-Dawley Rats" *Neurobiol. Aging* 9:691-696 (1988).

Bigl et al., "The Nucleus basalis of Meynert during ageing and in dementing neuropsychiatric disorders" *Brain Cholinergic Systems*, Steriade and Biesold, Oxford: Oxford University Press pp. 364-386 (1990).

Bothwell et al., "Dissociation Equilibrium Constant of β Nerve Growth Factor" *The Journal of Biological Chemistry* 252(23):8532-8536 (Dec. 10, 1977).

Canova-Davis et al., "Amino-terminal serine to glycine post-translational modification observed in nerve growth factor biosynthesized in Chinese hamster ovary cells" *Peptides* (Proceedings of the Thirteenth American Peptide Symposium Jun. 20-25, 1993). Hodges and Smith, Leiden The Netherlands: ESCOM pp. 230-231.

(Continued)

*Primary Examiner*—Robert C. Hayes
(74) *Attorney, Agent, or Firm*—Atulya R. Agarwal; Ginger R. Dreger; Heller Ehrman LLP

(57) ABSTRACT

NGF microencapsulation compositions having controlled release characteristics, preferably with increased stability, for the NGF component, particularly human recombinant NGF ("rhNGF") are provided that yield enhanced stability of NGF for use in promoting nerve cell growth, repair, survival, differentiation, maturation or function. Methods for making and using such compositions are also provided.

11 Claims, 7 Drawing Sheets

OTHER PUBLICATIONS

Cleland and Duenas, "Controlled Delivery of Nerve Growth Factor for Local Treatment of Neuronal Diseases" *Proceed. Intl. Symp. Control. Rel. Bioact. Mater.* pp. 823-824 (1997).

Cleland et al., "Stable Formulations of Recombinant Human Growth Hormone and Interferon-γ for Microencapsulation in Biodegradable Microspheres" *Pharm. Res.* 13(10): 1464-1475 (1996).

Connolly et al., "Pit Formation and Rapid Changes in Surface and Morphology of Sympathetic Neurons in Response to Nerve Growth Factor" *Journal of Cell Biology* 90:176-180 (Jul. 1981).

Davies, "The Neurochemistry of Alzheimer's Disease and Senile Dementia" *Med. Res. Rev.* 3:221-236 (1983).

De Young et al., "Temperature and pH Dependence of Recombinant Human Nerve Growth Factor Dimer Dissociation" *Biophys. Journal* 66(2):A401 (Feb. 1994).

Eppstein et al., "Biological Activity of Liposome-Encapsulated Murine Interferon γ Is Mediated by a Cell Membrane Receptor" *Proc. Natl. Acad. Sci.* 82(11):3688-3692 (1985).

Fischer et al., "NGF Improves Spatial Memory in Aged Rodents as a Function of Age" *J. Neurosci.* 11(7):1889-1906 (1991).

Frederickson et al., "Zinc-containing 7S-NGF Complex. Evidence From Zinc Histochemistry for Localization in Salivary Secretory Granules" *Journal of Histochemistry and Cytochemistry* 35(5):579-583 (1987).

Greene, "A Quantitative Bioassay for Nerve Growth Factor (NGF) Activity Employing a Clonal Pheochromocytoma Cell Line" *Brain Research* 133:350-353 (1977).

Halegoua et al., "Nerve Growth Factor Mediates Phosphorylation of Specific Proteins" *Cell* 22:571-581 (Nov. 1980).

Hefti, F., "Nerve Growth Factor Promotes Survival of Septal Cholinergic Neurons After Fimbrial Transections" *J. of Neuroscience* 6(8):2155-2162 (Aug. 1986).

Holland et al., "Nerve Growth Factor in Different Crystal Forms Displays Structural Flexibility and Reveals Zinc Binding Sites" *J. Mol. Biol.* 239:385-400 (1994).

Hwang et al., "Hepatic uptake and degradation of unilamellar sphingomyelin/cholesterol liposomes: a kinetic study" *Proc. Natl. Acad Sci.* 77:4030-4034 (1980).

Johnson et al., "A Month-Long Effect From a Single Injection of Microencapsulated Human Growth Hormone" *Nature Medicine* 2:795-799 (1996).

Koliatsos et al., "Human Nerve Growth Factor Prevents Degeneration of Basal Forebrain Cholinergic Neurons in Primates" *Ann. Neurol.* 30:831-840 (1991).

Koliatsos et al., "Recombinant Human Nerve Growth Factor Prevents Retrograde Degeneration of Axotomized Basal Forebrain Cholinergic Neurons in the Rat" *Exp. Neurol.* 112:161-173 (1991).

Korsching, S., "The role of nerve growth factor in the CNS" *TINS* pp. 570-573 (Nov./Dec. 1986).

Langer et al., "Biocompatibility of Polymeric Delivery Systems for Macromolecules" *J. Biomed. Mater. Res.* 15:267-277 (1981).

Langer, "Controlled Release of Macromolecules" *Chem. Tech.* 12:98-105 (1982).

Lofti et al., "Cerebral Ilemodynamic and Metabolic Effects of Chronic Alcoholism" *Cerebrovasc. and Brain Metab. Rev.* 1:2-25 (1989).

McDonald et al., "New Protein Fold Revealed by a 2.3-A Resolution Crystal Structure of Nerve Growth Factor" *Nature* 354:411-414 (1991).

Moore et al., "The Use of Hybrid Molecules in a Study of the Equilibrium Between Nerve Growth Factor Monomers and Dimers" *Neurobiology* 5:369-381 (1975).

Mumenthaler et al., "Feasibility Study on Spray-Drying Protein Pharmaceuticals: Recombinant Human Growth Hormone and Tissue-Type Plasminogen Activator" *Pharm. Res.* 11:12-20 (1994).

Petty et al., "The Effect of Systematically Administered Recombinant Human Nerve Growth Factor in Healthy Human Subjects" *Ann. Neurol.* 36:244-246 (1994).

Ross et al., "Zinc alters conformation and inhibits biological activities of nerve growth factor and related neurotrophins" *Nature Medicine* 3(8):872-878 (Aug. 1997).

Schmelzer et al., "Biochemical Characterization of Recombinant Human Nerve Growth Factor" *Journal of Neurochemistry* 59(5):1675-1683 (1992).

Scott et al., "Isolation and nucleotide sequence of a cDNA encoding the precursor of mouse nerve growth factor" *Nature* 302:538-540 (1983).

Shih et al., "Mutagenesis Identifies Amino-terminal Residues of Nerve Growth Factor Necessary for Trk Receptor Binding and Biological Activity" *Journal of Biological Chemistry* 269:27679-27686 (1994).

Sidman et al., "Controlled Release of Macromolecules and Pharmaceuticals from Synthetic Polypeptides Based on Glutamic Acid" *Biopolymers* 22(1):547-556 (1983).

Skaper et al., "Maintenance by Nerve Growth Factor of the Intracellular Sodium Environment in Spinal Sensory and Sympathetic Ganglionic Cells" *Brain Research* 197:379-389 (1980).

Thoenen et al., "Physiology of Nerve Growth Factor" *Physiological Reviews* 60(4):1284-1335 (Oct. 1980).

Tiercy et al., "Early Changes in the Synthesis of Nuclear and Cytoplasmic Proteins Are Induced by Nerve Growth Factor in Differentiating Rat PC12 Cells" *Journal of Cell Biology* 103(6):2367-2378 (Dec. 1986).

Timm et al., "Comparitive Equilibrium Denaturation Studies of the Neurotrophins: Nerve Growth Factor, Brain-derived Neurotrophic Factor, Neurotrophin 3, and Neurotrophin 4/5" *Biochemistry* 33:4667-4676 (1994).

Timm et al., "Equilibrium Denaturation Studies of Mouse β-nerve Growth Factor" *Protein Science* 1:236-244 (1992).

Tuszynski et al., "Recombinant Human Nerve Growth Factor Infusions Prevent Cholinergic Neuronal Degeneration in the Adult Primate Brain" *Ann. Neurol.* 30:625-636 (1991).

Ullrich et al., "Human β-Nerve Growth Factor Gene Sequence Highly Homologous to That of Mouse" *Nature* 303:821-825 (Jun. 1983).

Ullrich et al., "Sequence Homology of Human and Mouse B-NGF Subunit Genes" *Symp. on Quan. Biol.* 48:435-442 (1983).

Urfer et al., "Specificity Determinants in Neurotrophin-3 and Design of Nerve Growth Factor-Based trkC Agonists by Changing Central β-Strand Bundle Residues to Their Neurotrophin-3 Analogs" *Biochemistry* 36:4775-4781 (1997).

Urfer et al., "The Binding Epitopes of Neurotrophin-3 to its Receptors trkC and gp75 and the Design of a Multifunctional Human Neurotrophin" *The EMBO Journal* 13(24):5896-5909 (1994).

Williams, "Exogenous Nerve Growth Factor Stimulates Choline Acetyltransferase Activity in Aging Fischer 344 Male Rats" *Neurobiol. Aging* 12:39-46 (1991).

Yu et al., "Increased Phosphoylation of Specific Nuclear Proteins in Superior Cervical Ganglia and PC12 Cells in Response to Nerve Growth Factor" *Journal of Biological Chemistry* 255(21):10481-10492 (Nov. 10, 1980).

Palmer et al., *Arch. Biochem. Biophys.* 205:412-421 (1980).

```
┌─────────────────┐  SCREEN FORMULATIONS
│ PRODUCE SPRAY   │  FOR STABILITY DURING
│ FREEZE DRIED    │  DRYING AND SOLVENT
│ PROTEIN POWDER  │  TREATMENT
└────────┬────────┘
         │  ╭── RELEASE MODIFIERS
         │       (e.g. ZINC CARBONATE)
         ▼
┌─────────────────┐  PROTEIN AND RELEASE
│ HOMOGENIZE SOLID│  MODIFIER PARTICLE SIZE,
│ PROTEIN WITH PLGA│ AND AMOUNT OF MODIFIER
│ IN ORGANIC SOLVENT│ AFFECT FINAL PROPERTIES
└────────┬────────┘
         │ SPRAY
         │ MIXTURE
         ▼
┌─────────────────┐
│ SOLID ETHANOL WITH│
│ LIQUID NITROGEN. │                FINAL
│ WARMED TO -70°C, │  REMOVE EtOH   MICROSPHERES
│ ADD MORE ETHANOL │  AIR DRY       (20-90 μm)
└─────────────────┘
```

FIG._1

| SAMPLE | SEC % DIMER | % RECOVERY[a] | % RECEPTOR BINDING[b] |
|---|---|---|---|
| 5 mg/mL TREHALOSE / 0.01 % PEG | | | |
| PRE lyo | 99.62 | 102.8 | 89.2 |
| POST lyo 5°C, 1 WK | 99.49 | 102.9 | 95.7 |
| 4 WK | 99.64 | 102.1 | 89.2 |
| POST lyo 40°C, 1 WK | 99.77 | 102.9 | 90.7 |
| 4 WK | 99.76 | 101.8 | 84.4 |
| 5 mg/mL TREHALOSE IN 30 mM HISTIDINE | | | |
| PRE lyo | 99.57 | 102.5 | 90.7 |
| POST lyo 5°C, 1 WK | 99.19 | 103.5 | 105.7 |
| POST lyo 40°C, 1 WK | 99.72 | 103.1 | 83.3 |
| 4 WK | 99.69 | 102.2 | 87.6 |
| 5 mg/mL EACH TREHALOSE & SUCROSE | | | |
| PRE lyo | 99.58 | 103.2 | 94.4 |
| POST lyo 5°C, 1 WK | 99.53 | 103.1 | 96.2 |
| POST lyo 40°C, 1 WK | 99.76 | 102.9 | 82.1 |
| 4 WK | 99.77 | 101.9 | 87.1 |

[a] % RECOVERY = [SEC]/[UV]*100
[b] % RECEPTOR BINDING = [RRA]/[UV]*100

[UV] = ABSORBANCE AT 278 nm (1.45 mL/mg/cm)

*FIG._2*

| SAMPLE | SEC % DIMER | % RECOVERY[a] | % RECEPTOR BINDING[b] |
|---|---|---|---|
| 18.5 mg / mL SUCROSE / 39.3 mg / mL MANNITOL / 0.01% F68 | | | |
| PRE lyo | 99.47 | 103.7 | 98.2 |
| POST lyo 5°C, 1 WK | 99.44 | 103.1 | 85.0 |
| POST lyo 40°C, 1 WK | 99.69 | 103.4 | 85.8 |
| POST lyo 40°C, 4 WK | 99.78 | 103.4 | 91.5 |
| 20 mg / mL TREHALOSE / 5 mg / mL MANNITOL | | | |
| PRE lyo | 99.57 | 103.0 | 93.1 |
| POST lyo 5°C, 1 WK | 99.59 | 103.1 | 87.2 |
| POST lyo 5°C, 4 WK | 99.63 | 103.5 | 91.2 |
| POST lyo 40°C, 1 WK | 99.72 | 103.9 | 92.0 |
| POST lyo 40°C, 4 WK | 99.70 | 100.9 | 83.7 |
| [UV] = ABSORBANCE AT 278 nm (1.45 mL / mg / cm) | | | |

[a] % RECOVERY = [SEC] / [UV] * 100
[b] % RECEPTOR BINDING = [RRA] / [UV] * 100

FIG._3

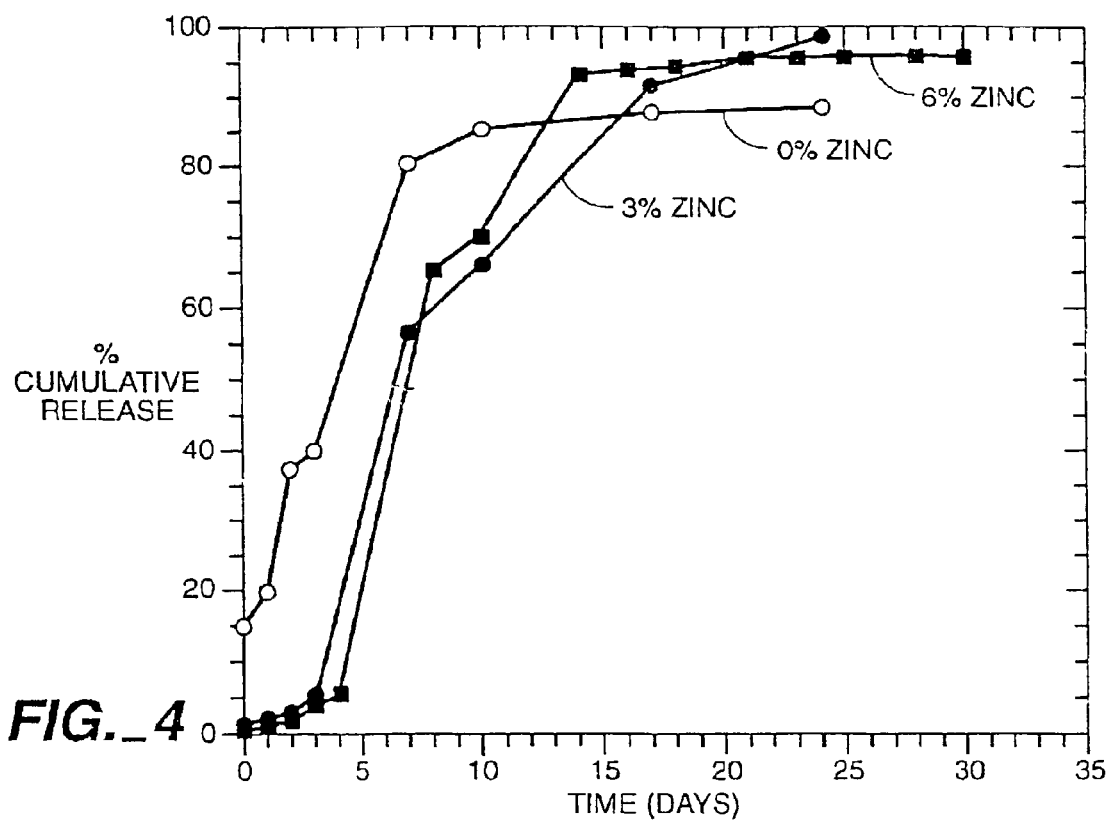
FIG._4
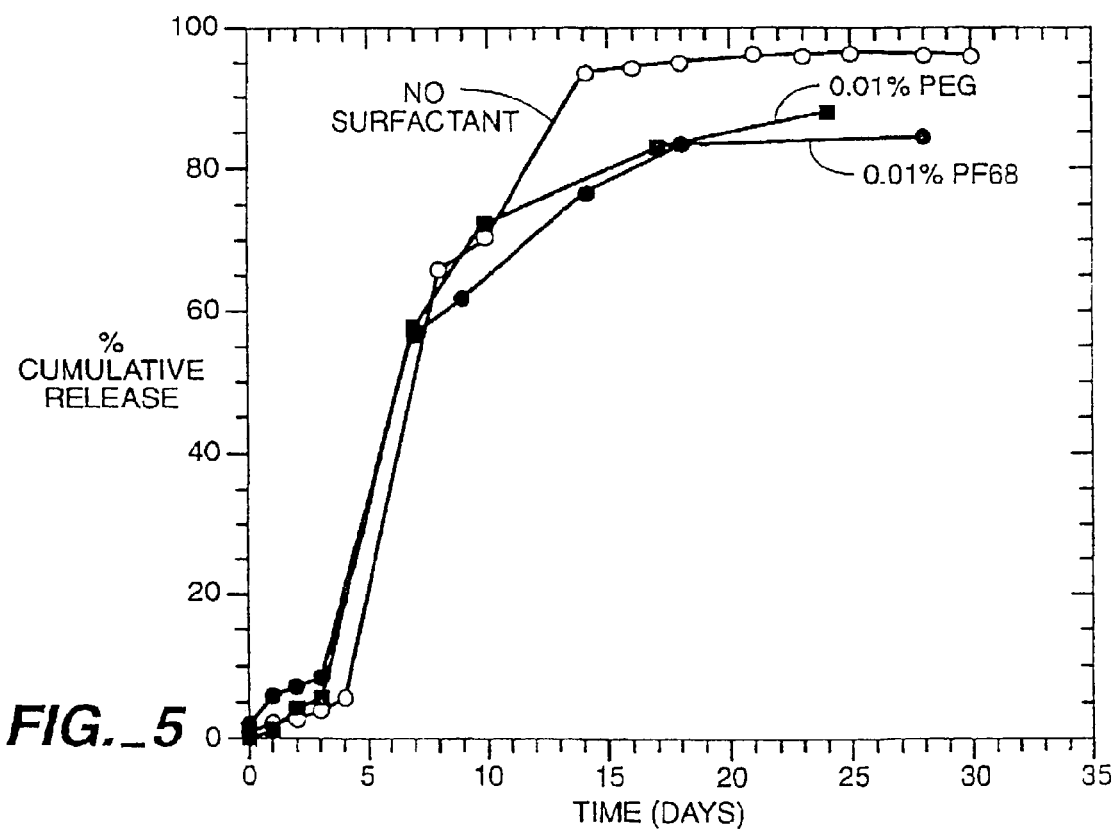
FIG._5

| rhNGF PLGA[a] | TIME | SEC[b] % DIMER | µg/ml | RRA[c] µg/ml | BCA[d] µg/ml |
|---|---|---|---|---|---|
| BATCH 1 | 1 HR 10 DAY | 93.93 85.87 | 85.9 529.2 | 48.6 ND | 138.3 593.8 |
| BATCH 1 | 1 HR 8 DAY | ND ~89 | ND ND | 24.7 76.6 | 42.9 128.2 |
| INITIAL PROTEIN | | | | 4750 | 5000[d] |
| DRY PROTEIN | | 99.53 | 743.9 | 695.0 | 757.8[d] |

A. MICROSPHERES PREPARED WITH 6% ZINC CARBONATE AT A rhNGF LOADING OF ~10% W/W. PROTEIN FORMULATION WAS 5 mg/mL EACH OF rhNGF AND TREHALOSE.

B. NATIVE SIZE EXCLUSION CHROMATOGRAPHY (SEC) TO MEASURE NATIVE DIMER (CONCENTRATION DETERMINED USING STANDARDS OF KNOWN CONCENTRATION).

C. PROTEIN CONCENTRATION BASED UPON RADIORECEPTOR ASSAY (RRA) USING rhNGF STANDARDS.

D. BICINCHONINIC ACID (BCA) MEASUREMENT OF PROTEIN CONCENTRATION USING rhNGF STANDARDS.

E. PROTEIN CONCENTRATION MEASURED BY ABSORBANCE AT 278 nm (E = 1.45 mL/mg/cm).

FIG._6

| FORMULATION | rhNGF: Zn ACETATE MOLAR RATIO (mM : mM) | LIQUID 5°C | LIQUID 37°C | LYOPHILIZED 5°C | LYOPHILIZED 37°C |
|---|---|---|---|---|---|
| 1 | 1 : 0 (0.189 : 0) | 99.6 | 92.2 | 99.7 | 99.8 |
| 2 | 1 : 4 (0.189 : 0.756) | 99.6 | 95.7 | 99.7 | 99.4 |
| 3 | 1 : 6 (0.189 : 1.134) | 99.6 | 96.9 | 99.7 | 99.3 |
| 4 | 1 : 8 (0.189 : 1.512) | 99.6 | 97.5 | 99.6 | 99.3 |
| 5 | 1 : 10 (0.189 : 1.890) | 99.7 | 97.8 | 99.8 | 99.4 |
| 6 | 1 : 14 (0.189 : 2.646) | 99.7 | 98.2 | 99.8 | 99.3 | rhNGF WAS FORMULATED AT 5 mg / mL (0.189 mM) IN 4 mM NaHCO₃ AT pH 7.4.

FIG._7

| FORMULATION | rhNGF: Zn ACETATE MOLAR RATIO | PROTEIN CONCENTRATION (mg / mL) LIQUID 5°C | LIQUID 37°C | LYOPHILIZED 5°C | LYOPHILIZED 37°C |
|---|---|---|---|---|---|
| 1 | 1 : 0 | 4.53 | 4.54 | 4.36 | 3.64 |
| 2 | 1 : 4 | 4.52 | 4.67 | 1.07 | 0.79 |
| 3 | 1 : 6 | 4.55 | 4.33 | 0.77 | 0.83 |
| 4 | 1 : 8 | 4.53 | 4.13 | 0.55 | 1.11 |
| 5 | 1 : 10 | 4.40 | 3.95 | 2.69 | 2.41 |
| 6 | 1 : 14 | 4.50 | 4.28 | 3.24 | 3.59 | rhNGF WAS FORMULATED IN 4 mM NaHCO₃ AT pH 7.4.

FIG._8

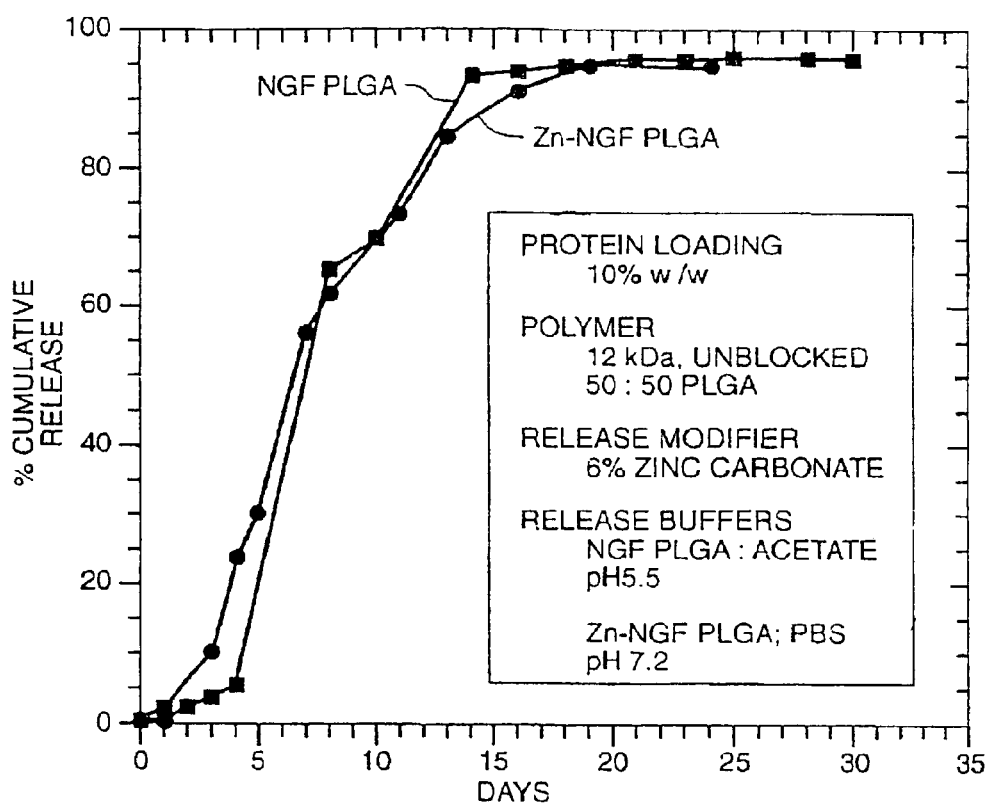
FIG._9
| FORMULATION | TIME | % DIMER | BUFFER[a] |
|---|---|---|---|
| rhNGF / PLGA | 1 HR | 94 | ACETATE, pH 5.5 |
| | 10 DAYS | 85 | |
| ZN : rhNGF / PLGA | 1 HR | 100 | PBS, pH 7.4 |
| | 10 DAYS | 93 | |
| LIQUID rhNGF | 4 WKS | 99 | HISTIDINE, pH 5.5 |
| LIQUID Zn : rhNGF | 4 WKS | 98 | BICARB., pH 7.4 |
[a] RELEASE BUFFERS FOR PLGA MICROSPHERES OR FORMULATION BUFFERS FOR rhNGF FORMULATED AS LIQUID. LIQUID FORMULATIONS WERE INCUBATED AT 37°C.
FIG._10

CONTROLLED RELEASE MICROENCAPSULATED NGF FORMULATION

CROSS-REFERENCE TO RELATED APPLICATIONS

This application is a continuation of U.S. patent application Ser. No. 09/095,911, filed Jun. 11, 1998, now U.S. Pat. No. 6,663,899 hereby incorporated by reference in its entirety and from which priority is claimed under 35 U.S.C. § 120, which non-provisional application was filed under 37 CFR 1.53(b)(1), claiming priority under 35 USC § 119(e) to provisional application No. 60/049,541 filed Jun. 13, 1997, the contents of which are incorporated herein by reference.

BACKGROUND

1. Field of the Invention

This invention relates to formulations of nerve growth factor ("NGF") and their use to induce nerve cell growth, differentiation, survival, repair, maturation, or function in vitro, in vivo or ex vivo. More particularly, this invention relates to microencapsulation compositions having controlled release characteristics, preferably with increased stability, for the NGF component, particularly human recombinant NGF ("rhNGF"). Methods for making and using such compositions are provided.

2. Description of Related Disclosures

Nerve growth factor (NGF) is a neurotrophic factor required for the growth and survival of sympathetic and sensory neurons during development and in mature animals (Thoenen, et al., *Physiol. Rev.* 60:1284–1335 (1980)). Clinical indications for recombinant human NGF include peripheral sensory neuropathy and Alzheimer's disease. For example, the systemic administration of NGF has been shown to reduce the sensory neuropathy induced by administration of cisplatin and taxol to mice (Apfel, et al., *Ann. Neurol.* 28:87–90 (1991); Apfel, et al., *Ann. Neurol.* 31:76–80 (1992)). In recent clinical trials, NGF has been administered to humans to improve sensory function in diabetic neuropathies (Petty, et al., *Ann. Neurol.* 36:244–246 (1994)). Although non-toxic and efficacious, administration of NGF in liquid parenteral formulation has been reported as associated with injection-site hyperalgesia and, particularly, myalgesia in current clinical trials.

Intracerebroventricular (ICV) administration of rhNGF can prevent degeneration of basal forebrain cholinergic neurons in rats and monkeys with fimbria-fornex lesions (Koliatsos, et al., *Exp. Neurol.* 112:161–73 (1991); Koliatsos, et al. Ann. Neurol. 30:831–40 (19991); Tuszynski, et al. Ann. Neurol. 30:626–36 (1991)). Studies have shown that ICV administration of rhNGF can enhance choline acetyltransferase activity and improve spatial memory in aging rats (Williams, *Neurobiol. Aging* 12:39–46 (1991); Fisher, et al., *J. Neurosci.* 11(7):1889–1906 (1991)). The ICV delivery of rhNGF across the blood-brain barrier has been accomplished by syringe, Ommaya® reservoir or Alzet pump. For the treatment of Alzheimer's disease, the use of implantable infusion pumps with catheters to deliver rhNGF continuously and directly to the ventricle of the brain has been considered. However, rhNGF has been observed to degrade via deamidation and iso-aspartate formation in some implantable pumps at 37° C. (physiological condition), as determined by RP-HPLC. The stability of NGF, particularly in liquid, is complicated beyond the usual chemical and physical degradation pathways as a result of the dimeric structure of NGF. Protein stability may be further complicated when recombinant protein is a mixture of C-terminally clipped NGF variants. While NGF normally exists as a dimer (the crystal structure of murine NGF shows 3 antiparallel pairs of b-strands forming a flat surface through which the monomers dimerize (McDonald, et al. *Nature* 354:411–414 (1991)); the dimer dissociation constant is $\leq 10^{-13}$ M (Bothwell et al., *J. Biol. Chem.* 252:8532–8536 (1977); Timm, et al., *Biochem.* 33:4667–4676 (1994)), higher order aggregation of NGF has been observed.

Thus, there exists a need for formulations containing NGF that maintain NGF stability and activity while providing a means for treating a variety of conditions, being effective for therapeutic administration to mammals, particularly human subjects, and particularly for intracerebral administration. The advantages of the present invention meet these needs and others as well.

SUMMARY

The present invention is based on the finding of formulation conditions and methods for controlled sustained release of NGF with low initial release rates and enhanced stability of NGF during the release period. A controlled sustained release formulation of NGF which provides a low initial release rate and retains enhanced stability of NGF is provided to effectively induce nerve cell growth, survival, differentiation, maturation, repair, or function, in vitro, in vivo or ex vivo. Provided is a controlled release formulation containing polymeric microspheres containing NGF, or its genetically engineered forms, especially human NGF, preferably the 118 form, that demonstrate very little loss of activity or aggregation during the release period. In preferred embodiments the formulations contain zinc-complexed NGF. In various embodiments the formulations, which have a controlled sustained release characteristic, have enhanced stability to agitation, freezing, thawing, light, or storage.

NGF polymeric controlled release systems are described wherein the NGF retains useful biological activity and is released over an extended period of time of at least one day, more typically one to two weeks, following administration. In the preferred embodiment, the NGF polymeric microspheres are made using very cold temperatures to freeze the polymer-NGF mixtures into polymeric microspheres with very high retention of biological activity and material. NGF is first preferably complexed in solution with a metal and, optionally, mixed with a stabilizing (and NGF-load-increasing) polyol, such as trehalose or mannitol, and dried, preferably spray freeze dried. The dried powder is mixed with a polymer, preferably a poly(lactide), or co-polymer, dissolved in a solvent such as ethyl acetate or methylene chloride. The polymer/NGF mixture is atomized into a vessel containing a frozen non-solvent such as ethanol, overlayed with a liquefied gas such as nitrogen, at a temperature below the freezing point of the polymer/active agent solution or suspension. The atomized particles freeze into microspheres upon contacting the cold liquefied gas, then sink onto the frozen non-solvent layer. The frozen non-solvent is then thawed. As the non-solvent thaws, the microspheres are still frozen and sink into the liquid non-solvent. The solvent in the microspheres also thaws and is slowly extracted into the non-solvent, resulting in hardened microspheres containing NGF.

Embodiments are provided in which sustained release of biologically active NGF from the microspheres, in vitro, ex vivo, or in vivo, extends over a period of one week to three months. The release profile can be achieved by inclusion of polymer degradation modifiers, pore forming agents, polymer-co-polymer ratios, and stabilizers of NGF, particularly zinc.

Also provided is a method for making controlled-release microspheres containing NGF or its genetically engineered forms, preferably metal-complexed, preferably with zinc, with very little loss-of activity or material during the formulation process. Provided are a method for making microspheres formed from a broad range of polymers which contain active NGF releasable in a controlled fashion, and the microspheres produced by such a process.

Provided herein is an NGF formulation with enhanced consistency for improved application to the neuron or mammal. A stable NGF formulation for use in treating a mammal, preferably human, in need of NGF treatment so as to provide a therapeutically effective amount of NGF, is provided. The microencapsulated devices also find use in cell culture methods, for example, with primary neuron cultures or neuronal cell lines. These and other aspects will become apparent to those skilled in the art in view of the present specification and drawings.

BRIEF DESCRIPTION OF THE DRAWINGS

FIG. 1 is a schematic depicting one embodiment for NGF microsphere production.

FIG. 2 depicts a preformulation screen of stability of spray freezed dried protein formulations:

FIG. 3 depicts additional preformulation screens of stability of spray freezed dried protein formulations.

FIG. 4 depicts the time course of release of rhNGF from PLGA microspheres containing different amounts of zinc carbonate: 0 (open circles), 3 (closed circles) or 6% (closed squares) w/w. Microspheres were incubated at pH 7.0 and 37° C. The release buffer was completely removed and replenished at each timepoint.

FIG. 5 depicts the time course of release of rhNGF from PLGA microspheres containing different amounts of surfactant: 0 (open circles), 0.01% PF68 (closed circles) or 0.01% PEG (closed squares) w/w. Microspheres were incubated at pH 7.0 and 37° C. The release buffer was completely removed and replenished at each timepoint.

FIG. 6 shows the stability of rhNGF released from one embodiment of PLGA microspheres where zinc was added after NGF was dried.

FIG. 7 shows the stability of NGF formulations containing zinc, as measured by percent monomer retained after four weeks.

FIG. 8 shows the protein concentration of NGF formulations containing zinc after four weeks.

FIG. 9 shows in vitro release of rhNGF from PLGA microspheres prepared with (closed circles) and without (closed squares) zinc acetate added to the protein formulation (preformulated with zinc). All microspheres were prepared using 12 KDa, unblocked 50:50 PLGA, and 10% (w/w) protein loading.

FIG. 10 depicts the effect of zinc-preformulation on stability of released rhNGF from PLGA microspheres.

DETAILED DESCRIPTION

The present invention is based on the discovery that NGF formulated with a metal, such as zinc, in a biopolymer microencapsulated form, has markedly low initial release rate from the microspheres, while allowing a controlled sustained release over a period of time greater than one day, and typically at least one to two weeks. Furthermore, formulation in aqueous solution of NGF with a metal that binds NGF, such as zinc, prior to encapsulation with biopolymer, surprisingly increased stability of NGF released from these microencapsulated devices Accordingly, in a preferred embodiment, the NGF is formulated with the metal in solution prior to drying or admixture with microencapsulaton polymers or release modifiers. While a few protein drugs have been formulated in a controlled release mode, controlled release at the desired rate and over a desired period is difficult to achieve. For example, it was reported that rhGH can form a complex with zinc and can be stabilized by complexing the protein with zinc acetate during microsphere fabrication process and during subsequent release in vivo (Johnson, et al. Nature Medicine 2:795–799(1996)). However, the conditions used to encapsulate a drug must not result in degradation of the drug to be delivered nor must the drug react with the polymeric matrix so as to inactivate or bind the drug. For a clinical situation, the delivery means must be cost effective to produce, stable to storage, and administrable using standard methodology. These needs have been met by the present invention.

"Polyol" as used herein denotes a hydrocarbon including at least two hydroxyls bonded to carbon atoms. Polyols may include other functional groups. Polyols are preferably of a molecular weight less than about 70,000 kD. Examples of polyols useful for practicing the instant invention include sugar alcohols such as mannitol and trehalose, and polyethers such as polyethylene glycol. See U.S. Pat. No. 5,589,167, issued Dec. 31, 1996, which is incorporated herein by reference. NGF can be stabilized against denaturation when treated with an organic solvent by admixing the polypeptide with a polyol, preferably a sugar alcohol, and more preferably trehalose, mannitol or sucrose, and most preferably trehalose.

"Polyether" as used herein denotes a hydrocarbon containing at least three ether bonds. Polyethers may include other functional groups. Polyethers useful for practicing the invention include polyethylene glycol (PEG).

"Dry polypeptide" as used herein denotes a polypeptide which has been subjected to a drying procedure such as lyophilization such that at least 50% of moisture has been removed.

"Encapsulation" as used herein denotes a method for formulating a therapeutic agent such as a polypeptide into a composition (microsphere device) useful for controlled release of the therapeutic agent. Examples of encapsulating materials useful in the instant invention include polymers or copolymers of lactic and glycolic acids, or mixtures of such polymers and/or copolymers, commonly referred to as "polylactides."

"Admixing" as used herein denotes the addition of an excipient to a polypeptide of interest, such as by mixing of dry reagents or mixing of a dry reagent with a reagent in solution or suspension, or mixing of aqueous formulations of reagents.

"Excipient" as used herein denotes a non-therapeutic agent added to a pharmaceutical composition to provide a desired consistency or stabilizing effect.

"Organic solvent" as used herein is intended to mean any carbon-based liquid solvent. Exemplary organic solvents include methylene chloride, ethyl acetate, dimethyl sulfoxide, tetrahydrofuran, dimethylformamide, and ethanol. As used herein, "alcohols" and "alcoholic solvents" are meant in the sense of the commonly used terminology for alcohol, preferably alcohols with 1 to 10 carbon atoms, more preferably methanol, ethanol, iso-propanol, n-propanol, or t-butanol, as well as glycerol, propylene glycol, ethylene glycol, hexylene glycol, polypropylene glycol, and polyethylene glycol, and most preferably ethanol or iso-propanol. Such alcohols are solvents that, when added to aqueous solution, increase the hydrophobicity of the solution by decreasing solution polarity.

"Treating" a polypeptide with an organic solvent as used herein refers to mixing a dry polypeptide with an organic solvent, or making an emulsion of a polypeptide in an aqueous formulation with an organic solvent, creating an interface between a polypeptide in an aqueous formulation with an organic solvent, or extracting a polypeptide from an aqueous formulation with an organic solvent.

"Microsphere" is used to mean solid spheres formed of polymer having NGF dispersed throughout, as well as microparticulates and microcapsules, unless otherwise noted. Microparticulates are specifically referred to when describing irregular shaped polymer or polymer-drug particles. Microcapsules are spherical shaped polymer devices having a non-polymer core or a core of a different polymer than the outer shell.

"Sustained" or "extended" release of NGF can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

"NGF" refers to nerve growth factor from any species, including murine, bovine, ovine, porcine, equine, avian, and preferably human, in native sequence or in genetically engineered variant form, and from any source, whether natural, synthetic, or recombinantly produced. Preferably, NGF is recombinantly produced. In a preferred method, the NGF is cloned and its DNA expressed, e.g., in mammalian cells, in bacterial cells.

Preferred for human use is human native-sequence, mature NGF, more preferably a 120 amino acid sequence, and even more preferably a 118 amino acid sequence form. The preferred amino acid sequence for human pre-pro-NGF and human mature NGF are provided by U.S. Pat. No. 5,288,622, which is specifically incorporated herein by reference. The 120 amino acid form, without additional post-translational modifications, is a preferred form in the homodimer form (i.e., 120/120). Even more preferred is the 118 form, without additional post-translational modifications, particularly as a homodimer (i.e., 118/118). The primary structure of a mammalian NGF (mouse NGF) was first elucidated by Angeletti and Bradshaw, *Proc. Natl. Acad. Aci. USA* 68:2417 (1971). The primary structure of its precursor, pre-pro-NGF, has been deduced from the nucleotide sequence of the mouse NGF cDNA (Scott et al. *Nature* 302:538 (1983); Ullrich et al. *Nature* 303:821 (1983)). The homologous human NGF (hNGF) gene has also been identified (Ullrich, *Symp. on Quan. Biol.*, Cold Spring Harbor 48:435 (1983); U.S. Pat. No. 5,288,622, issued Feb. 22, 1994, which is incorporated herein by reference). Its homology to the mouse NGF is about 90% and 87%, on the amino acid and nucleotide sequence levels, respectively. NGF can be glycosylated or unglycosylated.

In other embodiments the microsphere formulations of the present invention include NGF chimeric and pantropic neurotrophins, such as those reported in U.S. Pat. No. 5,488,099, issued Jan. 30, 1996, in Urfer et al., *EMBO J.* 13(24): 5896–909 (1994), and in WO 95/33829, published Dec. 14, 1995 (incorporated herein by reference) in which the NGF has been modified to bind to more than one receptor or contains a receptor binding activity not normally present to a significant degree in the native NGF. Of particular interest are chimeras having an NGF amino acid backbone but modified to bind receptors other than trkA, such as trkB or trkC. These NGF forms have an amino acid sequence homologous (usually greater than 80%, preferably greater than 90%, and more preferably greater than 95%, and most preferably greater than 97%) to the amino acid sequence of NGF, with substitutions which confer other neurotrophin specificities. In the preferred embodiment, the domains are substituted for NGF residues; that is, some number of amino acids are deleted from the NGF sequence, and an identical or similar number of amino acids are substituted, conferring an additional specificity. For example, a pantropic NGF is made with a D16A substitution, which confers BDNF specificity (trkB-binding activity), while retaining trkA-binding activity. Preferred are those in which amino acid substitutions have been made in NGF with an amino acid from a corresponding position in NT-3 that is responsible for binding the trkC receptor for NT-3. Such NGF mutants have NT-3-like trkC receptor binding activity while retaining NGF conformation, pharmacokinetics and purification behavior (Urfer, et al., *Biochemistry* 36(16):4775–4781 (1997)). For example, substitutions in the pre-variable region 1 (V18E+V20L+G23T) and in variable region 4 (Y79Q+T81K+H84Q+F86Y+K88R) trkC-binding activity. The substitutions in the pre-variable region 1 can be made with only single amino acid substitutions in variable region 4; for example, V18E+V20L+G23T and one or more of Y79Q, T81K, H84Q, F86Y, or K88R may be made. These NGF mutants can also be engineered to lack trkA binding activity, for example, by removing or modifying the N-terminal 1 to 9 amino acids of NGF. The 109 amino acid species (10–118) hNGF, resulting from the loss of the first 9 residues of the N-terminus and the last two residues from the C-terminus of purified recombinant human NGF, is 300-fold less efficient in displacing mouse [$^{125}$I]NGF from the human trkA receptor compared to (1–118)hNGF (Shih et al., *J. Biol. Chem.* 269 (44):27679–86 (1994)). Such NGF genetically engineered mutants—that bind trkC but not trkA—are particularly preferred for use in the invention described herein.

The isolation of a recombinant human NGF involves separation of the protein from a variety of diverse host cell contaminants. Each step involves special buffers that enable sufficient separation to take place. The final or penultimate processing step for NGF is complicated by the presence of several NGF variants that co-purify using conventional chromatographic media. When a refolding step is included in the recovery and purification process, the variants include misfolded forms of NGF. Variants can also include those that differ chemically from NGF, such as carbamylated, amidated, deamidated or proteolytically cleaved forms. In the case of NGF, these species consist primarily of dimeric forms—homodimers, e.g., 120/120 or 117/117, when 118/118 is desired, or heterodimers, e.g., 120/118, 117/118—or chemically modified variants—isoaspartate, mono-oxidized, glycosylation variants, N-terminal and C-terminal truncated forms, and dimers thereof (Schmelzer et al. (*J. Neurochem.* 59:1675–1683 (1992)); Canova-Davis, et al., In Peptides: Chemistry, Structure and Biology, Escom Science Publishers, Leiden, The Netherlands, pp. (1993) (Proceedings of the Thirteenth American Peptide Symposium, Edmonton, Alberta, Canada, Jun. 20–25, 1993)). Preferred formulations are substantially pure and homogeneous 118/118 NGF without these modifications.

By "substantially pure" is meant a degree of purity of total NGF to total protein where there is at least 70% neurotrophin, more preferably at least 80%, and even more preferably increasing to at least 90%, 95% or 99%. A particularly preferred purity is at least 95%. By "essentially pure" is meant that the composition is at least 90% or more pure for the desired neurotrophin.

By "substantially free of NGF variants" is meant a composition in which the percent of desired NGF species to total NGF (including less desirable NGF species) is at least 70% desired NGF species, more preferably at least 80%, and even more preferably increasing to at least 90%, 93%, 95% or 99%. By "essentially free" is meant that the composition contains at least 90% or more desired NGF. A particularly preferred level is at least 95% desired neurotrophin, e.g., correctly folded, intact 118/118 rhNGF, species. The undesirable species or forms may be misprocessed forms or chemical variants, e.g. charge variants, resulting from the fermentation or purification process, or preferably all of the foregoing, as disclosed herein. For example, when NGF is folded in vitro after synthesis in bacteria, NGF "species" or "variants" can include misfolded or partially folded forms.

By "misfolded" variant is meant a variant of the NGF which differs from the parental NGF by the pairing of its cysteine residues or by the particular cysteine residues which are free or blocked. Misfolded variants can also have the same cysteine pairing as the parental NGF but have a different three dimensional conformation resulting from misfolding.

By "chemical" variant is meant a variant that differs chemically from the desirable parental NGF, for example by carbamylation, amidation, or proteolytic cleavage.

The NGF, preferably metal-stabilized as taught herein, is formulated for sustained release, preferably by microencapsulation, preferably with a biodegradable polymer, as a microsphere. Suitable examples of sustained-release preparations include semipermeable matrices of solid hydrophobic polymers containing NGF, which matrices are in the form of shaped articles, e.g. films, or microcapsules. Examples of sustained-release matrices include polyesters, hydrogels [e.g., poly(2-hydroxyethyl-methacrylate) as described by Langer, et al., *J. Biomed. Mater. Res.*, 15:167–277 (1981) and Langer, *Chem. Tech.*, 12:98–105 (1982) or poly(vinylalcohol], polylactides (U.S. Pat. No. 3,773,919, EP 58,481), copolymers of L-glutamic acid and gamma ethyl-L-glutamate (Sidman, et al., *Biopolymers*, 22:547–556 [1983]), non-degradable ethylene-vinyl acetate (Langer, et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133,988). While polymers such as ethylene-vinyl acetate and lactic acid-glycolic acid enable release of molecules for over 100 days, certain hydrogels release polypeptides for shorter time periods. When encapsulated polypeptides remain in the body for a long time, they may denature or aggregate as a result of exposure to moisture at 37° C., resulting in a loss of biological activity and possible changes in immunogenicity. As has been determined herein, preformulation of NGF with a metal remarkedly maintains the integrity of NGF during sustained release.

Alternative sustained-release modes for which the NGF or NGF-metal complex provides an advantage include liposomally entrapped metal-stabilized NGF. Liposomes containing polypeptides are prepared by methods known per se: DE 3,218,121; Epstein, et al., *Proc. Natl. Acad. Sci. USA*, 82:3688–3692 (1985); Hwang, et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal ligand analogs therapy. Liposomes with enhanced circulation time are disclosed in U.S. Pat. No. 5,013,556.

The compositions hereof including lyophilized forms, are prepared in general by compounding the components using generally available pharmaceutical compounding techniques, known per se. Likewise, standard lyophilization procedures and equipment well-known in the art are employed.

The biodegradable polymer of the present invention has low water soluability or is water-insoluble, and includes aliphatic polyesters, e.g., homopolymers or copolymers synthesized from one or more kinds of α-hydroxycarboxylic acids (e.g., glycolic acid, lactic acid, 2-hydroxybutyric acid, valinic acid, leucic acid, etc.), hydroxydicarboxylic acids (e.g., malic acid, etc.), hydroxytricarboxylic acids (e.g., citric acid, etc.), or their mixtures; poly-α-cyanoacrylic esters, e.g., poly(methyl α-cyanoacrylate), poly(ethyl α-cyanoacrylate), poly(butyl α-cyanoacrylate), etc.; and amino acid polymers, e.g., poly(γ-benzyl-L-glutamate) etc., or their mixtures. The mode of polymerization for these biodegradable polymer may be any of random, block or graft polymerizations technique.

The preferred biodegradable polymers are aliphatic polyesters, e.g., homopolymers or copolymers synthesized from one or more kinds of α-hydroxycarboxylic acids (e.g., glycolic acid, lactic acid, 2-hydroxybutyric acid, etc.), hydroxydicarboxylic acids (e.g., malic acid, etc.) and hydroxytricarboxylic acids (e.g., citric acid, etc.), or their mixtures, and so on.

Among the above-mentioned aliphatic polyesters, the homopolymers and copolymers synthesized from one or more kinds of the α-hydroxycarboxylic acids are preferable in view of biodegradability and biocompatibility. Particularly preferred aliphatic polyesters are copolymers synthesized from two or more kinds of the α-hydroxycarboxylic acids. Furthermore, these copolymers can be used as mixtures.

When the α-hydroxycarboxylic acids are chiral compounds, they may be any of D-, L- and D-, L-configuration. It is preferable that the ratio of the D-/L-configuration (mol %) is in the range of about 75/25 to about 25/75. More preferred is a hydroxycarboxylic acid wherein the ratio of the D-/L-configuration (mol %) is in the range of about 60/40 to about 30/70.

An example of the above mentioned α-hydroxycarboxylic acid polymer is a lactic acid polymer (hereinafter sometimes referred to as "polylactic acid"). The α-hydroxycarboxylic acid copolymer includes copolymers of glycolic acid with the other α-hydroxycarboxylic acids such as lactic acid and 2-hydroxybutyric acid. Preferred α-hydroxycarboxylic acid copolymers are lactic acid-glycolic acid copolymer and 2-hydroxybutyric acid-glycolic acid copolymer. A particularly preferred α-hydroxycarboxylic acid copolymer is a lactic acid-glycolic acid copolymer.

The polylactic acid may be either D-configuration or L-configuration or a mixture; one with the D-/L-configuration ratio (mol %) of about 75/25 to about 20/80 is preferred. More preferred is a polylactic acid wherein the ratio of the D-/L-configuration (mol %) is in the range of about 60/40 to about 25/75. Most preferred is a polylactic acid wherein the ratio of D-/L-configuration is in the range of about 55/45 to about 25/75.

The polylactic acid preferably has the weight average molecular weight, as defined below, of about 1,500 to about 10,000. More preferred is a polylactic acid having the weight average molecular weight of about 2,000 to about 8,000. Particularly preferred is a polylactic acid having the weight average molecular weight of about 3,000 to about 6,000. The dispersity (weight average molecular weight/number average molecular weight) of polylactic acid is preferably in the range of about 1.2 to about 4.0, and more preferably in the range of about 1.5 to about 3.5.

The polylactic acid can be produced by the prior art methods described in EP-172636 (e.g., by dehydrative polycondensation in the absence of a catalyst or by dehydrative polycondensation in the presence of an inorganic solid acid catalyst). The preferred polylactic acid is produced by dehydrative polycondensation in the absence of a catalyst.

The compositional ratio (lactic acid/glycolic acid, mol %) in the lactic acid-glycolic acid copolymer is about 100/0 (homopolymer) to about 40/60, preferably about 90/10 to about 45/55, more preferably about 75/25 to 50/50, and most preferably about 60/40 to about 40/60. The weight average molecular weight of the lactic acid-glycolic acid copolymer is preferably about 3,000 to about 20,000, and more preferably about 4,000 to about 15,000. The dispersity (weight average molecular weight/number average molecular weight) of the lactic acid-glycolic acid copolymer is preferably about 1.2 to about 4.0, and more preferably about 1.5 to about 3.5. In the present invention, two kinds of lactic acid-glycolic acid copolymers differing in compositional ratio and weight average molecular weight can be used in an admixture of any ratio. The typical example is a mixture of a lactic acid-glycolic acid copolymer wherein the compositional ratio of the lactic acid/glycolic acid (mol %) is about 75/25 and the weight average molecular weight is about 6,000. Another example is lactic acid-glycolic acid copolymer wherein the compositional ratio of the lactic acid/glycolic acid (mol %) is about 50/50 and the weight average molecular weight is about 4,000. The preferred weight ratio of the mixture is about 25/75 to about 75/25.

The lactic acid-glycolic acid copolymers can be produced by the known methods described in EP-172636 (e.g., dehydrative polycondensation in the absence of a catalyst or dehydrative polycondensation in the presence of an inorganic solid acid catalyst). The preferred copolymer is one produced by dehydrative polycondensation in the absence of a catalyst.

The compositional ratio of the 2-hydroxybutyric acid-glycolic acid copolymer is about 10 to about 75 mol % of glycolic acid and the remaining mol % of 2-hydroxybutyric acid, more preferably about 20 to about 75 mol % of glycolic acid, and more preferably about 30 to about 70 mol % of glycolic acid. The weight average molecular weight of 2-hydroxybutyric acid-glycolic acid copolymer is preferably about 2,000 to about 30,000, and more preferably about 3,000 to about 20,000. The particularly preferred weight average molecular weight of the copolymer is about 4,000 to about 15,000. The dispersity (weight average molecular weight/number average molecular weight) of 2-hydroxybutyric acid-glycolic acid copolymer is preferably about 1.2 to about 4.0, and more preferably about 1.5 to about 3.5.

2-Hydroxybutyric acid-glycolic acid copolymers can be produced by the known methods described in EP-172636 (e.g., dehydrative polycondensation in the absence of a catalyst or dehydrative polycondensation in the presence of an inorganic solid acid catalyst). The preferred copolymer is one produced by dehydrative polycondensation in the absence of a catalyst.

The glycolic acid copolymers (e.g., lactic acid-glycolic acid copolymer, 2-hydroxybutyric acid-glycolic acid copolymer, etc.) may be used in an admixture with polylactic acid. When glycolic acid copolymer is used in combination with polylactic acid, the ratio of glycolic acid copolymer/polylactic acid (weight %) may be, for example, about 10/90 to about 90/10. The preferred ratio is about 20/80 to about 80120, and the most preferred ratio is about 30/70 to about 70/30.

The terms "weight average molecular weight" and "number average molecular weight" as used in this specification mean the polystyrene equivalent average molecular weight and number average molecular weight of a sample as determined by gel permeation chromatography (GPC) using 9 polystyrene standards having the weight average molecular weights of 120,000, 52,000, 22,000, 9,200, 5,050, 2,950, 1,050, 580 and 162. These determinations can be made using GPC Column KF804L×2 (Showa Denko K.K.), RI Monitor L-3300 (Hitachi, Ltd.), and chloroform as the mobile phase.

In the present invention, biodegradable polymers synthesized by the dehydrative polycondensation reaction in the absence of a catalyst have free carboxyl groups at the terminus. Such biodegradable polymers having free carboxyl groups at the terminus feature a high correlation between the number average molecular weight determined by end-group titrimetric assay and the number average molecular weight determined by GPC assay using polystyrene standards of known molecular weights, as previously described.

By the end-group assay method, the number average molecular weight can be determined in the following manner. About 1 g to 3 g of the biodegradable polymer is dissolved in a mixed solvent of acetone (25 ml) and methanol (5 ml), and the carboxyl groups in the solution are quickly titrated with 0.05N alcoholic potassium hydroxide solution using phenolphthalein as indicator under stirring at room temperature (about 0 to about 30° C.). The number average molecular weight is calculated by the following equation: Number average molecular weight by end-group assay=20000 (A/B), where A is the weight mass (g) of biodegradable polymer and B is the amount (ml) of 0.05N alcoholic KOH solution added until end-point is reached.

In the case of a biodegradable polymer having free carboxyl groups at the terminal which is synthesized from one or more kinds of α-hydroxy acids by dehydrative polycondensation in the absence of a catalyst, a high correlation is found between the number average molecular weight determined by GPC assay and the number average molecular weight determined by the end-group assay. In contrast, in the case of a biodegradable polymer produced from the cyclic dimer of an α-hydroxy acid by the ring-opening polymerization method using a catalyst and having essentially no free carboxyl groups at the terminus, the number average molecular weight found by the end-group assay is considerably higher than the number average molecular weight found by GPC. Because of this difference, a biodegradable polymer having free carboxyl groups at the terminal can easily be differentiated from a biodegradable polymer not having free carboxyl groups at the terminus.

Whereas the number average molecular weight found by the end-group assay is an absolute value, the number average molecular weight found by GPC assay is a relative value dependent on many variables such as analytical methods and conditions (e.g., the types of mobile phase and column, reference standard, choice of slicing width, selection of baseline, etc.) and, therefore, is hard to generalize. However, a high correlation exists between the number average molecular weight found by end-group assay and the number average molecular weight found by the GPC assay when the value obtained from the end-group assay is within the range of about 0.5 to about 2.0 times the value found by the GPC assay. The preferred range is about 0.8 to about 1.5 times. That the number average molecular weight found by end-group assay is "considerably higher" than the number average molecular weight found by GPC means that the value found by the end-group assay is more than about twice the value found by the GPC assay.

In the present invention, the preferred polymers are those showing a high correlation between the number average molecular weight found by the end-group assay and the number average molecular weight found by the GPC assay.

The metal salts which can be used for converting a biodegradable polymer to its metal salt is not particularly limited as far as it does not exert unwanted or deleterious influences in vivo. The metal salt includes a salt formed by a monovalent metal such as alkali metals (e.g., sodium, potassium, etc.) or alkaline earth metals (e.g., calcium, magnesium, etc.), or a polyvalent metal such as zinc (II), iron (II, III), copper (II), tin (II, IV), and aluminum (II, III) with an inorganic acid or an organic acid.

The metal is preferably a polyvalent metal, and more preferably alkaline earth metals and zinc. Particularly preferred metals are calcium and zinc.

Inorganic acids that may be used in the metal salt formation include hydrogen halide (e.g., hydrochloric acid, hydrobromic acid, hydroiodic acid, hydrofluoric acid), sulfuric acid, nitric acid, thiocyanic acid, and so on.

Organic acids that may be used in the metal salt formation include aliphatic carboxylic acids and aromatic acids. Preferred aliphatic carboxylic acids are $C_{1-9}$ aliphatic carboxylic acids, e.g., aliphatic monocarboxylic acids, aliphatic dicarboxylic acids, and aliphatic tricarboxylic acids. The aliphatic carboxylic acids may be saturated or unsaturated.

The aliphatic monocarboxylic acids include $C_{1-9}$ saturated aliphatic monocarboxylic acids (e.g., carbonic acid, acetic acid, propionic acid, butyric acid, valeric acid, caproic acid, enanthoic acid, caprylic acid, pelargonic acid, capric acid, etc.) and $C_{2-9}$ unsaturated aliphatic monocarboxylic acids (e.g., acrylic acid, propiolic acid, methacrylic acid, crotonic acid, isocrotonic acid, etc.).

The aliphatic dicarboxylic acids include $C_{2-9}$ saturated aliphatic dicarboxylic acids (e.g., malonic acid, succinic acid, glutaric acid, adipic acid, pimellic acid, etc.) and $C_{2-9}$ unsaturated aliphatic dicarboxylic acids (e.g., maleic acid, fumaric acid, citraconic acid, mesaconic acid, etc.).

The aliphatic tricarboxylic acids include $C_{2-9}$ saturated aliphatic tricarboxylic acids (e.g., tri-carvallylic acid, 1,2,3-butanetricarboxylic acid, etc.).

The above-mentioned aliphatic carboxylic acids additionally may have 1 or 2 hydroxyl groups. Illustrative examples are glycolic acid, lactic acid, glyceric acid, tartronic acid, malic acid, tartaric acid, citric acid, and so on.

Preferred aliphatic carboxylic acids are aliphatic monocarboxylic acids. More preferred aliphatic carboxylic acids are $C_{2-9}$ aliphatic monocarboxylic acids. Particularly preferred are $C_{2-3}$ saturated aliphatic monocarboxylic acids. The most preferred aliphatic carboxylic acid includes acetic acid.

Aromatic acids that may be used in the metal salt formation include benzoic acid, salicylic acid and phenolsulfonic acid.

The metal salt of the biodegradable polymer, may also be obtained using the acetylacetonate or oxide of the above-mentioned polyvalent metals. Preferred metal donors of the type are zinc acetylacetonate and zinc oxide.

Metal salts which can be used for converting a biodegradable polymer to its metal salt are preferably the salt formed by a polyvalent metal with an organic or inorganic acid (hereinafter referred to as a polyvalent metal salt).

Polyvalent metal salt that may be used include salts of zinc with an inorganic acid, e.g., zinc halides (e.g., zinc chloride, zinc bromide, zinc iodide, zinc fluoride), zinc sulfate, zinc nitrate, zinc thiocyanate, etc.; salts of zinc with an organic acid, e.g., aliphatic carboxylic acid zinc salts (e.g., zinc carbonate, zinc acetate, zinc glycolate, zinc lactate, zinc tartrate, etc.), aromatic zinc salts (e.g., zinc benzoate, zinc salicylate, zinc phenolsulfonate, etc.); salts of calcium with an inorganic acid, e.g., calcium halide (e.g., calcium chloride, calcium bromide, calcium iodide, calcium fluoride, etc.), calcium sulfate, calcium nitrate, calcium thiocyanate, etc.; salts of calcium with an organic acid, e.g., aliphatic carboxylic acid calcium salt (e.g., calcium carbonate, calcium acetate, calcium propionate, calcium oxalate, calcium tartrate, calcium lactate, calcium citrate, calcium gluconate, etc.) and aromatic calcium salts (e.g., calcium benzoate, calcium salicylate, etc.). Preferred salts are zinc acetate, zinc carbonate, calcium acetate, and calcium carbonate. The more preferred polyvalent metal salt includes zinc acetate and calcium acetate.

If necessary, in order to form a homogeneous NGF/metal complex, the metals occurring in the bioactive polypeptide from purification may be removed from the polypeptide by known methods and replaced with the stabilizing metal of choice.

In the present invention, it is preferable that additives other than the biodegradable polymer metal salt in the sustained-release preparation do not form a metal salt.

The biodegradable polymer metal salt in the present invention can be produced by emulsifing and dispersing an aqueous solution or solid form of a metal salt in an organic solvent solution of a biodegradable polymer to prepare a water/oil (w/o) or oil/water (o/w) emulsion or an organic solution or suspension of a biodegradable polymer containing a metal salt. The resulting substances are washed and dried or subjected to an in-water drying method, phase separation method, spray drying method or the like with washing and drying. The metal salt which does not participate in the formation of a salt with the biodegradable polymer in this process is preferably removed.

The organic solvent mentioned above preferably has a boiling point not exceeding 120° C. Such organic solvent includes halogenated hydrocarbons (e.g., dichloromethane, chloroform, carbon tetrachloride, etc.), alcohols (e.g., ethanol, methanol, etc.), acetonitrile, and so on. These solvents can also be used as a mixture. The preferred organic solvents are dichloromethane and acetonitrile. Particularly preferred is dichloromethane.

The metal content of the biodegradable polymer metal salt is preferably about 0.01 to about 10% (w/w), more preferably about 0.05 to about 7% (w/w), and most preferably about 0.1 to about 5% (w/w). The metal content of a biodegradable polymer metal salt can be determined by atomic absorption spectrometry.

Methods for producing a biodegradable polymer metal salt (e.g., in-water drying method, phase separation method and spray drying method) are described below.

To produce a biodegradable polymer metal salt by an in-water drying method (water/oil/water or w/o/w method), the biodegradable polymer is first dissolved in an organic solvent to prepare an organic solvent solution (hereinafter referred to sometimes as the oil phase). The concentration of the biodegradable polymer in this organic solvent solution is suitably selected according to the molecular weight of the polymer and the kind of organic solvent used. For example, the concentration of the biodegradable polymer in the organic solvent may be about 0.01 to about 90% (w/w), preferably about 0.1 to about 80% (w/w), and more preferably about 1 to about 70% (w/w). For the internal aqueous phase, an aqueous solution of metal salts is used. The metal salt concentration may be from about 10 to about 90% (w/v), and preferably about 20 to about 80% (w/v). However, the metal salt concentration depends on the solubility of the metal salt in water. The above metal salt aqueous solution is dispersed and emulsified in the organic solvent solution of the biodegradable polymer to provide a w/o emulsion. The volume ratio of the aqueous solution of metal salts in the organic solvent solution of the biodegradable polymer is about 1:1,000 to about 1:1, preferably about 1:100 to about 1:2, and most preferably about 1:50 to about 1:3. Emulsification can be achieved by conventional emulsification methods such as by using a turbine mixer, a homogenizer or the like.

The w/o emulsion thus obtained is then added to an aqueous phase (the external aqueous phase) to give a w/o/w emulsion. Then the oil-phase solvent is evaporated off to provide the desired biodegradable polymer metal salt. The volume of the external aqueous phase may be selected from the range of, for example, about 1 to about 10,000 times the volume of the oil phase. The preferred range is about 2 to about 5,000 times, and the most preferred range is about 5 to about 2,000 times. Solvent evaporation can be achieved by commonly used methods, including the method in which the solvent is evaporated under normal or gradually reduced pressure while stirring using a propeller stirrer or a magnetic stirrer, etc., and the method in which the solvent is evaporated while the degree of vacuum is adjusted using a rotary evaporator, and so on.

An emulsifier may be added to the external aqueous phase. The emulsifier may be any substance capable of providing for stable w/o/w emulsions. Examples of such emulsifiers include anionic surfactants, nonionic surfactants, polyoxyethylene-caster oil derivatives, polyvinylpyrrolidone, polyvinyl alcohol, carboxymethylcellulose, lecithin, gelatin, hyaluronic acid and so on. The preferred emulsifier is polyvinyl alcohol. Multiple emulsifiers may also be used in combination for use in the external aqueous phase. The concentration of the emulsifier based on the external aqueous phase may be selected from the range of about 0.001 to about 20% (w/w). The preferred range is about 0.01 to about 10% (w/w) and the still more preferred range is about 0.05 to about 5% (w/w).

A metal salt which is similar to or different from the metal salt contained in the internal aqueous phase may also be added to the external aqueous phase. In such cases, preferably a fatty acid metal salt is added in such an amount that the concentration of the metal salt in the external aqueous phase is about 0.01 to 20% (w/w) or more preferably about 0.1 to 10% (w/w). By careful selection of the concentration of the metal salt in the external aqueous phase, the transfer of the metal salt used in the internal aqueous phase from the biodegradable polymer into the external aqueous phase may be avoided.

The biodegradable polymer metal salt thus produced is recovered by centrifugation or filtration, washed with distilled water several times to remove the emulsifier and other deposits from the salt surface, then redispersed in distilled water, and lyophilized.

To produce a biodegradable polymer metal salt by an in-water drying method (oil/water method), a solution of the biodegradable polymer in an organic solvent is first prepared as in method (A). Then, the metal salt is added, and dispersed or dissolved in the organic solvent solution of biodegradable polymer. The ratio of metal salt to biodegradable polymer (by weight) is about 5:1 to about 1:100, preferably about 2:1 to about 1:50, and more preferably about 1:1 to about 1:10. The organic solvent solution thus obtained is then poured into an aqueous phase and an o/w emulsion is prepared by using a turbine mixer or the like. Then, the oil-phase solvent is evaporated as in method (A) to provide the biodegradable polymer metal salt. The volume of the aqueous phase is based on the volume of oil phase and is selected from the range of, for example, about 1 to about 10,000 times the volume of the oil phase, or preferably about 2 to about 5,000 times. The most preferred range is about 5 to about 2,000 times.

As in method (A), an emulsifier may be added into this aqueous phase.

A metal salt may be added into the aqueous phase that is similar to or different from the metal salt which is added, and dispersed or dissolved in the oil phase.

The biodegradable polymer metal salt thus produced is separated, washed and lyophilized as in method (A).

To produce a biodegradable polymer metal salt by a phase separation method (coacervation method), a coacervating agent is gradually added into the water/oil emulsion as used in method (A) or the organic solvent solution of biodegradable polymer containing the metal salt as used in method (B) under stirring to precipitate and solidify the biodegradable polymer metal salt. The amount of coacervating agent used is based on the volume of the w/o emulsion or organic solvent solution of the biodegradable polymer. The volume used is about 0.01 to about 1,000 times the volume of the W/O emulsion or organic solution of the biodegradable polymer, preferably about 0.05 to about 500 times, and more preferably about 0.1 to about 200 times.

The coacervating agent may be a substance belonging to any of the categories of polymers, mineral oils or vegetable oils, which are miscible with the organic solvent used for dissolving the biodegradable polymer, but in which the biodegradable polymer is not appreciably soluble. Typical examples are silicone oil, sesame oil, soybean oil, corn oil, cottonseed oil, coconut oil, linseed oil, mineral oil, n-hexane, n-heptane, and so on. The coacervating agents can be used in a combination of two or more kinds.

The biodegradable polymer metal salt thus produced is recovered by filtration and washed repeatedly with heptane or the like to remove the coacervating agent. The salt is then washed as in method (A) and lyophilized.

In the production of a biodegradable polymer metal salt by the in-water drying method or coacervation method, an antiflocculant may be added for preventing agglomeration of the particles. Antiflocculants that may be used include a water-soluble polysaccharides, such as mannitol, lactose, glucose, and starches (e.g., corn starch), hyaluronic acid and its alkali metal salt, glycine, a protein such as fibrin, collagen and an inorganic salt such as sodium chloride, sodium hydrogen phosphate, and so on.

To produce a biodegradable polymer metal salt by a spray drying method, either a water/oil emulsion prepared from an aqueous solution of the metal salt and an organic solvent solution of the biodegradable polymer, or an organic solvent solution or suspension of biodegradable polymer containing the metal salt, is sprayed via a nozzle into the drying chamber of a spray drier to volatilize the organic solvent in fine droplets in a very short time, and a fine biodegradable polymer metal salt is produced. Examples of the above-mentioned nozzle are a binary-fluid nozzle, a pressure nozzle and a rotary disk nozzle. An aqueous solution of the above-described antiflocculant also may be sprayed via another nozzle in order to prevent agglomeration of biodegradable polymer metal salt with the w/o emulsion or the organic solvent solution or suspension of the biodegradable polymer containing the metal salt. The biodegradable polymer metal salt thus produced is washed as in method (A) and, if necessary, further subjected to removal of water and organic solvent under heating and reduced pressure.

The sustained-release preparation of the present invention can be manufactured by dispersing NGF in an organic solvent containing the biodegradable polymer metal salt, and subjecting the resulting dispersion to formulation. The manufacturing method of the present invention can be used with the above-described (A) in-water drying method (w/o/w method), (B) in-water drying method (o/w method), (C) phase separation method (coacervation method), (D) spray drying method, or any modification thereof. The organic solvent in the organic solvent solution is preferably a solvent with a boiling point not higher than 120° C. Such organic solvent includes halogenated hydrocarbons (e.g., dichloromethane, chloroform, carbon tetrachloride, etc.), alcohols (e.g., ethanol, methanol, 1,4-butanediol, 1,5-pentanediol, etc.) and acetonitrile, among others. Any of the solvents can be used together as a mixture. When a single organic solvent is to be employed, dichloromethane or acetonitrile is particularly preferred. When a mixture of organic solvents is to be employed, a combination of a halogenated hydrocarbon (e.g., dichloromethane) with acetonitrile or an alcohol (e.g., methanol, ethanol, etc.) is preferred. Particularly preferred in many instances is a combination of dichloromethane with acetonitrile. The ratio (by volume) of the halogenated hydrocarbon to either acetonitrile or alcohol is about 40:1 to about 1:1 and preferably about 20:1 to about 1:1.

The manufacturing method for sustained-release preparation is now described using microspheres as an example.

To produce a sustained or controlled release microsphere preparation using the in-water drying method (w/o/w method), an organic solvent solution of the biodegradable polymer metal salt is first prepared in the same manner as in method (A) described above. The concentration of the biodegradable polymer metal salt in the organic solvent solution is dependent on the type and molecular weight of biodegradable polymer metal salt and the type of the organic solvent. For example, the ratio of biodegradable polymer metal salt to organic solvent may be about 0.01 to about 80% (w/w), and is preferably about 0.1 to about 70% (w/w), and most preferably about 1 to about 60% (w/w). For the internal aqueous phase, an aqueous solution of NGF is used. The concentration of NGF in aqueous solution may be for example, about 0.1% (w/v) to about 500% (w/v), preferably about 1% (w/v) to about 400% (w/v) and more preferably about 10% (w/v to about 300% (w/v). To this aqueous solution may be added pH adjusting agent (e.g., acetic acid, hydrochloric acid, sodium hydroxide, etc.), stabilizers (e.g., serum albumin, gelatin, etc.), and/or preservatives (e.g., p-hydroxybenzoic acid esters, etc.). The aqueous solution thus obtained is dispersed in the organic solvent solution of biodegradable polymer metal salt to provide a w/o emulsion.

The ratio (v/v) of aqueous solution of NGF (dimer form) to organic solvent solution of biodegradable polymer metal salt is about 1:1,000 to about 1:1, preferably about 1:100 to about 1:5, and more preferably about 1:50 to about 1:5, while even more preferably about 1:50 to about 1:10, and most preferably about 1:50 to about 1:20. Ranges of 1:4 to 1:50, 1:6 to 1:20, and 1:8 to 1:14 are useful embodiments, with 1:50 to 1:20 being particularly preferred. Several useful ratio embodiments are 1:10, 1:15, 1:20, and 1:25. The w/o emulsion thus obtained is then poured in an aqueous phase (external aqueous phase) to give a w/o/w emulsion and the solvent in the oil phase is evaporated to provide microspheres. An emulsifier may be added to the external aqueous phase. The emulsifier can be any substance that is generally capable of providing a stable w/o/w emulsion. Specifically, anionic surfactants, nonionic surfactants, polyoxyethylene-caster oil derivatives, polyvinylpyrrolidone, polyvinyl alcohol, carboxymethylcellulose, lecithin, gelatin, hyaluronic acid, etc., may be employed. The preferred emulsifier is polyvinyl alcohol. Two or more kinds of emulsifiers can be used in combination. The concentration of the emulsifier based on the external aqueous phase is chosen from a range of about 0.001% (w/w) to about 20% (w/w), preferably about 0.01% (w/w) to about 10% (w/w), and more preferably about 0.05% (w/w) to about 5% (w/w). A metal salt, whether the same salt as that added to the internal aqueous phase or a different salt, can be added to the external aqueous phase. In this procedure, preferably a fatty acid metal salt is added so that the metal salt concentration of the external aqueous phase will be about 0.01% to about 20% (w/w) and preferably about 0.1% to about 10% (w/w). By changing the metal salt concentration of the external aqueous phase, the metal salt used in the internal aqueous phase can be prevented from migrating from the biodegradable polymer into the external aqueous phase.

The microspheres thus produced are recovered by centrifugation or filtration, washed with distilled water repeatedly to remove the emulsifier and other deposits from the capsule surface, then redispersed in distilled water or the like, and lyophilized. Then, if necessary, residual water and organic solvent in the microspheres are further removed by heating under reduced pressure. The microspheres are heated at a temperature not below the glass transition temperature of the biodegradable polymer and not so high as to cause aggregation of the microspheres. The heating temperature is preferably selected within the range from the glass transition temperature of the biodegradable polymer to about 30° C. higher than the glass transition temperature of the biodegradable polymer. Here, glass transition temperature is defined as the intermediate glass transition temperature determined using a differential scanning calorimeter during heating at a rate of 10 or 20° C. per minute.

To produce a sustained or controlled release microsphere preparation using the in-water drying method (o/w method), an organic solvent solution of the biodegradable polymer metal salt is first prepared in the same manner as in method (A). The concentration of the biodegradable polymer metal salt in the organic solvent may be similar to that described in method (i). In the organic solvent solution of the biodegradable polymer metal salt thus obtained is added and dissolved or dispersed NGF to prepare an organic solvent solution or suspension containing the biodegradable polymer metal salt and NGF. The weight ratio of NGF to the biodegradable polymer metal salt may for example be about 1:1000 to about 1:1, preferably about 1:200 to about 1:5 and more preferably about 1:100 to about 1:5, with about 1:50 to about 1:5 being more preferable, while even more preferable is about 1:50 to about 1:10, and most preferable being about 1:50 to about 1:20. Ranges of 1:4 to 1:50, 1:6 to 1:20, and 1:8 to 1:14 are useful embodiments, with 1:50 to 1:20 being particularly preferred. Several useful ratio embodiments are 1:10, 1:15, 1:20, and 1:25.

This organic solvent solution containing the biodegradable polymer metal salt and NGF is poured into an aqueous phase to prepare an oil/water emulsion. The solvent in the oil phase is then evaporated off to provide microspheres.

The microspheres thus obtained are recovered, washed and lyophilized as in method (i). Thereafter the microspheres may be heated under reduced pressure to remove the residual water and organic solvent as in method (i).

To produce a sustained or controlled release microsphere preparation using the phase separation method, a coacervating agent is gradually added to the same w/o emulsion as used in method (i) or the same organic solvent solution of biodegradable polymer metal salt and NGF as used in method (ii) under stirring in the same manner as in method (C) to afford precipitated and solidified microspheres. The microspheres thus produced are recovered and washed to remove the coacervating agent and free NGF as in method (C). Then, if necessary, the residual water and organic solvent within the microspheres are removed by heating under reduced pressure in the same manner as in method (i).

In the production of microspheres by the in-water drying method or phase separation method, an antiflocculant may be added for preventing agglomeration of particles as in method (C).

To produce a sustained or controlled release microsphere preparation using the spray-drying method, same w/o emulsion as used in method (i) or the same organic solvent solution containing the biodegradable polymer metal salt and NGF as used in method (ii) is sprayed via a nozzle in the same manner as in method (D) to provide microspheres. If necessary, the microspheres thus obtained are heated under reduced pressure to remove residual water and organic solvent as in method (i).

In a preferred embodiment, NGF is formulated in aqueous solution with a metal (in salt form) that binds NGF, such as zinc as zinc acetate or zinc carbonate, prior to further formulation with other release modifiers, degradable biopolymers forming the microsphere, or the like. The NGF-metal aqueous solution buffer is sufficiently non-acid to allow the metal to bind to NGF. Preferably the pH is 6.5 to 8.5, more preferably 7 to 8 and even more preferably 7.2 to 7.6. Since the NGF-binding metal provides a means to stabilize released NGF, as well as reduce initial release rates from the microsphere, the addition of a stabilizing polyol, such as trehalose, to the aqueous NGF-metal solution prior to freeze-drying is optional.

The freeze dried NGF-zinc powder is processed into a controlled release microsphere as taught herein, preferably as discussed in Example 1. Because metal was added to the NGF aqueous solution, the addition of a metal as a release modifier, to the dried powder prior to or with admixture with a biodegradable polymer is optional. However, when present the release modifier is preferably a metal ion salt in which the metal binds NGF, such as an alkali metal, alkaline earth metal, or a polyvalent metal, as discussed herein, more preferably the release modifier is zinc, and the release modifier 1 to 10% by weight, more preferably 3 to 6% by weight.

The metal salts which can be used for aqueous formulation with NGF are those that bind NGF and stabilize it upon release from the microsphere. The salt is not particularly limited as far as it does not exert unwanted or deleterious influences in vivo. The metal salt includes a salt formed by a monovalent metal such as alkali metals (e.g., sodium, potassium, etc.) or alkaline earth metals (e.g., calcium, magnesium, etc.), or a polyvalent metal such as zinc (II), iron (II, III), copper (II), tin (II, IV), and aluminum (II, III) with an inorganic acid or an organic acid. The metal is preferably a polyvalent metal, and more preferably alkaline earth metals and zinc. Particularly preferred metals are calcium and zinc. Inorganic acids that may be used in the metal salt formation include hydrogen halide (e.g., hydrochloric acid, hydrobromic acid, hydroiodic acid, hydrofluoric acid), sulfuric acid, and so on. Organic acids that may be used in the metal salt formation include aliphatic carboxylic acids and aromatic acids. Preferred aliphatic carboxylic acids are $C_{1-9}$ aliphatic carboxylic acids, e.g., aliphatic monocarboxylic acids, aliphatic dicarboxylic acids, and aliphatic tricarboxylic acids. The aliphatic carboxylic acids may be saturated or unsaturated. The aliphatic monocarboxylic acids include $C_{1-9}$ saturated aliphatic monocarboxylic acids (e.g., carbonic acid, acetic acid, propionic acid, butyric acid, valeric acid, caproic acid, enanthoic acid, caprylic acid, pelargonic acid, capric acid, etc.) and $C_{2-9}$ unsaturated aliphatic monocarboxylic acids (e.g., acrylic acid, propiolic acid, methacrylic acid, crotonic acid, isocrotonic acid, etc.). The aliphatic dicarboxylic acids include $C_{2-9}$ saturated aliphatic dicarboxylic acids (e.g., malonic acid, succinic acid, glutaric acid, adipic acid, pimellic acid, etc.) and $C_{2-9}$ unsaturated aliphatic dicarboxylic acids (e.g., maleic acid, fumaric acid, citraconic acid, mesaconic acid, etc.). The aliphatic tricarboxylic acids include $C_{2-9}$ saturated aliphatic tricarboxylic acids (e.g., tri-carvallylic acid, 1,2,3-butanetricarboxylic acid, etc.). The above-mentioned aliphatic carboxylic acids additionally may have 1 or 2 hydroxyl groups. Illustrative examples are glycolic acid, lactic acid, glyceric acid, tartronic acid, malic acid, tartaric acid, citric acid, and so on. Preferred aliphatic carboxylic acids are aliphatic monocarboxylic acids. More preferred aliphatic carboxylic acids are $C_{2-9}$ aliphatic monocarboxylic acids. Particularly preferred are $C_{2-3}$ saturated aliphatic monocarboxylic acids. The most preferred aliphatic carboxylic acid includes acetic acid. Aromatic acids that may be used in the metal salt formation include benzoic acid, salicylic acid and phenolsulfonic acid. Metal salts for in solution formulation with NGF are preferably the salt formed by a polyvalent metal with an organic or inorganic acid (hereinafter referred to as a polyvalent metal salt).

Polyvalent metal salt that may be used include salts of zinc with an inorganic acid, e.g., zinc halides (e.g., zinc chloride, zinc bromide, zinc iodide, zinc fluoride), zinc sulfate, zinc nitrate, zinc thiocyanate, etc.; salts of zinc with an organic acid, e.g., aliphatic carboxylic acid zinc salts (e.g., zinc carbonate, zinc acetate, zinc glycolate, zinc lactate, zinc tartrate, etc.), aromatic zinc salts (e.g., zinc benzoate, zinc salicylate, zinc phenolsulfonate, etc.); salts of calcium with an inorganic acid, e.g., calcium halide (e.g., calcium chloride, calcium bromide, calcium iodide, calcium fluoride, etc.), calcium sulfate, calcium nitrate, calcium thiocyanate, etc.; salts of calcium with an organic acid, e.g., aliphatic carboxylic acid calcium salt (e.g., calcium carbonate, calcium acetate, calcium propionate, calcium oxalate, calcium tartrate, calcium lactate, calcium citrate, calcium gluconate, etc.) and aromatic calcium salts (e.g., calcium benzoate, calcium salicylate, etc.). Preferred salts are zinc acetate, zinc carbonate, calcium acetate, and calcium carbonate. The more preferred polyvalent metal salt includes zinc acetate and calcium acetate.

The molar ratio of NGF to metal is that which stabilizes NGF upon release from the microspheres without causing untoward harm or side-effect in a patient or cell culture to which the NGF-microspheres are administered. The in solution molar ratio of NGF to metal ion can range from 1 to 4 to 1 to 50, more preferably 1 to 6 to 1 to 20, even more preferably 1 to 8 to 1 to 14.

If necessary, in order to form a homogeneous NGF/metal complex, any metals occurring in the NGF from purification may be removed from the polypeptide by known methods and replaced with the stabilizing metal of choice.

Optionally present in the NGF and metal salt mixture is an excipient useful to either stabilize NGF against denaturation by organic solvent used in the miroencapsulation process and/or to maximize NGF concentration. Typically the excipient will be a polyol of a molecular weight less than about 70,000 kD. Examples of polyols that maybe used include trehalose, mannitol, and polyethylene glycol. Typically, the mass ratio of trehalose to polypeptide will be 100:1 to 1:100, preferably 1:1 to 1:10, more preferably 1:3 to 1:4. Typical mass ratios of mannitol to polypeptide will be 100:1 to 1:100, preferably 1:1 to 1:10, more preferably 1:1 to 1:2. Typically, the mass ratio of PEG to polypeptide will be 100:1 to 1:100, preferably 1:1 to 1:10. Optimal ratios are chosen on the basis of an excipient concentration which allows maximum solubility of polypeptide with minimum denaturation of the polypeptide.

In the present invention, it is preferable that the efficiency of entrapment of NGF into a biodegradable polymer greater than or equal to 50%. More preferably it is greater than or equal to 80% and most preferably it is greater than or equal to 90%.

The concentration of bioactive NGF loaded in the sustained-release preparation in the present invention can range from 0.001 to 50% by weight of the microsphere, about 0.01 to about 30% (w/w) preferred, with 2 to 20 percent more preferred, and 5 to 15% even more preferred. A load of about 10% (w/w) is typical. NGF loading is limited by the solubility of the NGF in water and the volume of aqueous NGF that can be added to the polymer in organic solvent. Volumes of greater than 0.5 mL of NGF per gram of polymer typically result in a large initial burst of drug from the microspheres. To avoid these difficulties, a solid drug formulation can be used in place of the aqueous drug solution. Thus, a solid-in-oil-in-water process are preferred to produce microspheres with high drug loading (greater then 10%) with low to moderate initial bursts. The solid drug formulation used for microencapsulation must be stable in organic solvents and it must have a small size (1–5 μm) relative to the final desired microspheres (10–100 μm) to permit high loading and low burst of the drug. For protein formulations, one method of obtaining small dried solids is spray drying. Mummenthaler et al. (*Pharm. Res.* 11(1):12–20 (1994)) describe spray drying rhGH formulations. Since rhGH is easily denatured by surface interactions such as air-liquid interfaces, the spray drying of rhGH must be performed with surfactants in the rhGH formulation. Unexpectedly, as taught herein the presence of a metal was found capable to stabilize NGF during freeze-drying without the need for surfactants.

The sustained-release preparation may be administered in the form of microsphere or in various dosage forms such as non-oral preparations (e.g., intramuscular-, subcutaneous- or visceral-injectable or indwellable preparation; nasal-, rectal- or uterine-transmucosal preparation), or oral preparations (e.g., capsules such as hard capsule and soft capsule, solid preparations such as in granules and powder, liquid preparations such as a suspension).

The particularly preferred sustained-release preparation is by injection. To prepare an injection using the microspheres obtained above, the microspheres may be formulated with a viscous physiologically acceptable solution: a dispersant (e.g., surfactants such as Tween 80, HCO-60; polysaccharides such as carboxymethylcellulose, sodium alginate, sodium hyaluronate; protamine sulfate; polyethylene glycol 400, etc.), a preservative (e.g., methyl paraben, propyl paraben, etc.), an isotonizing agent (e.g., sodium chloride, mannitol, sorbitol, glucose, dextran, etc.), and a local anesthetic (e.g., xylocaine hydrochloride, chlorobutanol, etc.) to provide an aqueous suspension, or dispersed with vegetable oil (e.g., sesame oil, corn oil, etc.), or a mixture thereof with a phospholipid (e.g., lecithin) or medium-chain fatty acid triglycerides (e.g., Migriol 812) to provide an oily suspension.

When the sustained-release preparation is microspheres, the microspheres are preferably fine particle. The size of microspheres for an injectable suspension may be selected from the range satisfying the requirements for the degree of dispersion and passage through the needle used for the injection. For example, the microcapsule particle size may be within the range of about 0.1 to about 300 μm, preferably about 1 to about 150 μM, more preferably about 2 to about 100 μm, and most preferably about 20 to 90 microns.

Methods of preparing microspheres as a sterile preparation include, but are not limited to, the method in which the entire production process is sterile, the method in which gamma rays are used as the sterilant, and method in which an antiseptic is added during the manufacturing process.

The sustained-release preparation can be safely used in mammals (e.g., humans, bovine, swine, dogs, cats, mice, rats, rabbits, etc.) with low toxicity. A "patient" for the purposes of the present invention includes both humans and other mammals. Thus the methods are applicable to both human therapy and veterinary applications.

The sustained-release preparation of the invention is useful to prevent or treat neuronal damage. Nerve growth factor has prominent effects on sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes, in the state of phosphorylation of neuronal proteins, and in the abundance of certain mRNAs and proteins likely to play a role in neuronal differentiation and function. (Connolly et al., *J. Cell. Biol.* 90:176–180 (1981); Skaper and Varon, *Brain Res.* 197:379–389 (1980); Yu, et al., *J. Biol. Chem.* 255:10481–10492 (1980); Haleqoua and Patrick, *Cell* 22:571–581 (1980); Tiercy and Shooter, *J. Cell. Biol.* 103: 2367–2378 (1986)). Forebrain cholinergic neurons also respond to NGF and may require NGF for trophic support. (Hefti, *J. Neurosci.*, 6:2155 (1986)). Indeed, the distribution and ontogenesis of NGF and its receptor in the central nervous system (CNS) suggest that NGF acts as a target-derived neurotrophic factor for basal forebrain cholinergic neurons (Korsching, TINS, pp 570–573 (November/December 1986)).

Accordingly, NGF formulations of the invention are believed to be useful in promoting the development, maintenance, or regeneration of neurons in vivo, including central (brain and spinal chord), peripheral (sympathetic, parasympathetic, sensory, and enteric neurons), and motorneurons. NGF formulations of the invention are utilized in methods for the treatment of a variety of neurologic diseases and disorders. In a preferred embodiment, the formulations of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's chorea, stroke, ALS, peripheral neuropathies, and other conditions characterized by necrosis or loss of neurons, whether central, peripheral, or motorneurons, in addition to treating damaged nerves due to trauma, burns, kidney disfunction, injury, and the toxic effects of chemotherapeutics used to treat cancer and AIDS. For example, peripheral neuropathies associated with certain conditions, such as neuropathies associated with diabetes, AIDS, or chemotherapy may be treated using the formulations of the present invention. It also is useful as a component of culture media for use in culturing nerve cells in vitro or ex vivo.

In various embodiments of the invention, NGF formulations are administered to patients in whom the nervous system has been damaged by trauma, surgery, stroke, ischemia, infection, metabolic disease, nutritional deficiency, malignancy, or toxic agents, to promote the survival or growth of neurons, or in whatever conditions have been found treatable with NGF. For example, NGF formulation of the invention can be used to promote the survival or growth of motorneurons that are damaged by trauma or surgery. Also, NGF formulations of the invention can be used to treat motoneuron disorders, such as amyotrophic lateral sclerosis (Lou Gehrig's disease), Bell's palsy, and various conditions involving spinal muscular atrophy, or paralysis. NGF formulations of the invention can be used to treat human neurodegenerative disorders, such as Alzheimer's disease, Parkinson's disease, epilepsy, multiple sclerosis, Huntington's chorea, Down's Syndrome, nerve deafness, and Meniere's disease. NGF formulations of the invention can be used as cognitive enhancer, to enhance learning particularly in dementias or trauma. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al. in Brain Cholinergic Systems, M. Steriade and D. Biesold, eds., Oxford University Press, Oxford, pp. 364–386 (1990)). And there are a number of other neurotransmitter systems affected by Alzheimer's disease (Davies Med. Res. Rev. 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al. Neurobiol. Aging 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., Cerebrovase. and Brain Metab. Rev 1:2 (1989)). Such dementias can be treated by administration of NGF formulations of the invention.

Further, NGF formulations of the invention are preferably used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to diabetic peripheral neuropathy, distal sensorimotor neuropathy, AIDS-associated neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

A therapeutically effective dose of an NGF formulation is administered to a patient. By "therapeutically effective dose" herein is meant a dose that produces the effects for which it is administered or that amount which provides therapeutic effect in a particular administration regimen. Dosage of the sustained-release preparation is that needed to achieve an effective concentration of NGF in vivo, for the particular condition treated, though the dosage varies with the type of NGF variant, the desired duration of the release, the target disease, the subject animal species and other factors, such as patient condition. The exact dose will depend on the disorder to be treated, and will be ascertainable by one skilled in the art using known techniques. Currently, rhNGF has been administered subcutaneously to patients having diabetic- or AIDs-related peripheral neuropathy, with Phase III trials in progress. The weekly dosage amounts used in these clinical studies provides a good starting point for the clinician to determine dosages for administration of microencapsulated NGF of the invention. In general, the NGF formulations of the present invention are administered at about 0.01 µg NGF/kg body weight to about 100 mg/kg per day, preferably from 0.02 to 10 mg/kg, more preferably 0.03 to 500 ug/kg, and most preferably 0.5 ug/kg to 100 ug/kg. In some embodiments doses of 0.03 to 1.0 ug/kg, more preferably 0.1 to 0.3 ug/kg, are given. In addition, as is known in the art, adjustments for age as well as the body weight, general health, sex, diet, time of administration, drug interaction and the severity of the disease may be necessary, and will be ascertainable with routine experimentation by those skilled in the art. Typically, the clinician will administer NGF formulations of the invention until a dosage is reached that repairs, maintains, and, optimally, reestablishes neuron function. The progress of this therapy is easily monitored by conventional assays.

Results from Phase II clinical trials indicate that patients with peripheral neuropathy disease require three dosings per week of rhNGF at either 0.3 or 0.1 µg/kg. This means that only 21 or 7 μg per dosing of rhNGF is needed for an average patient of body weight 70 kg. The current rhNGF liquid formulation is 2 mg/mL in 10 mM sodium acetate, pH 5.5, 142 mM NaCl. This dosing information provides a starting point for dosing with the NGF microsphere device.

When the sustained-release preparation is a one-week-long action formulation, the dosage of NGF can be chosen from the range of about 0.0001 to about 10 mg/kg body weight per an adult. The more preferred dosage can be suitably chosen from the range of about 0.0005 to about 1 mg/kg body weight. The preferred administration frequency of the sustained-release preparation may be suitably chosen from once a week to once every two weeks depending on the type of NGF polypeptide, the dosage form, the duration of the release, the target disease, the subject animal species and other factors.

The compositions herein are prepared containing amounts of NGF microspheres to yield in resuspendend form NGF concentrations from 0.07 to 20 mg/ml, preferably 0.08 to 15 mg/ml, more preferably 0.09 to 10 mg/ml, and most preferably 0.1 to 2 mg/ml. In a preferred embodiment the NGF concentration is 0.1 mg/ml. In another preferred embodiment the NGF concentration is 2.0 mg/ml. For use of these compositions in administration to human patients suffering from peripheral neuropathies, for example, these compositions may contain from about 0.1 mg/ml to about 2 mg/ml NGF, corresponding to the currently contemplated dosage rate for such treatment. NGF is well-tolerated and higher doses can be administered if necessary as determined by the physician.

The sustained-release preparation is preferably stored dry at room temperature or in the cold. More preferably, the sustained-release preparation is stored in the cold. "Room temperature" means 15° to 25° C., and "cold" means a temperature below 15° C.

Therapeutic NGF compositions generally are placed into a container having a sterile access port, for example, an intravenous solution bag or vial having a stopper pierceable by a hypodermic injection needle.

In another embodiment of the invention is provided a kit for NGF administration, which includes a vial or receptacle containing a sustained release device of the invention that contains a pharmaceutically effective amount of nerve growth factor, preferably complexed with a metal, more preferably with zinc. Optionally provided is a sterile, viscous, physiologically acceptable solution for resuspendnig the microspheres. For example, a volume of 1.5 ml is convenient when 0.3 ug/kg or 0.1 ug/kg dosages are used.

NGF optionally is combined with or administered in concert with other neurotrophic factors including NT-4/5, NT-3, and/or BDNF and is used with other conventional therapies for nerve disorders.

An effective amount of the microspheres containing NGF are administered to a patient by injection subcutaneously, intramuscularly, intraperitoneally, and intradermally, by administration to mucosal membranes (such as intranasally or by means of a suppository), or by in situ delivery to provide the desired dosage of NGF based on the known parameters for treatment with NGF of the various medical conditions. Accordingly, administration of the formulations of the present invention can be done in a variety of ways, including, but not limited to, orally, subcutaneously, intravenously, intracerebrally, intranasally, transdermally, intraperitoneally, intramuscularly, intrapulmonary, vaginally, rectally, intraventricularly, intrathecally, or intraocularly. The formulations can be administered continuously by infusion into the fluid reservoirs of the CNS, although bolus injection is acceptable, using techniques well known in the art, such as pumps, reservoirs or implantation. Particularly preferred is intracerebroventricular (ICV) administration of rhNGF by syringe, Ommaya® reservoir, Alzet pump or the like. In some instances, for example, in the treatment of wounds, the formulations may be directly applied as a solution or spray. The microspheres can also be pressed into a pellet of desired shape for implantation.

For an injectable, the microspheres are sieved, preferably to a 20 to 90 micron size. The bulk, sieved microspheres are vialed in an amount suitable for resuspension and injection. Suspension of the microspheres is done with a sterile solution with suitable viscosity to facilitate injection while maintaining an even suspension of the particles to avoid settling during re-suspension mixing, dose withdrawal, and injection. A suitable viscosity is one similar to that of a 5% dextran-70 solution. For subcutaneous injection the microspheres can be resuspended in 5% dextran-70 in saline solution (9% NaCl) with optional 0.01% Tween 20.

In general, the formulations of the subject invention may contain other components in amounts not detracting from the preparation of stable forms and in amounts suitable for effective, safe pharmaceutical administration. For example, other pharmaceutically acceptable excipients well known to those skilled in the art may form a part of the subject compositions. These include, for example, various bulking agents, additional buffering agents, chelating agents, antioxidants, cosolvents and the like; specific examples of these could include trihydroxymethylamine salts ("Tris buffer"), and disodium EDTA. Optionally, formulations of NGF can contain physiologically acceptable carriers, a preservative, a buffer or buffers, an excipient or multiple excipients, such as polyethylene glycol (PEG) in addition to trehalose or mannitol, or a nonionic surfactant such as Tween® surfactant, or stabilizers (*Remington's Pharmaceutical Sciences*). Acceptable carriers, excipients or stabilizers are nontoxic to recipients at the dosages and concentrations employed and will not significantly decrease NGF stability in the formulations as taught herein. Such compounds include antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as histidine, methionine, glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or non-ionic surfactants which include a polysorbate, such as polysorbate 20 or 90 (Tween), etc., the poloxamers, such as poloxamer 184 or 188, Pluronic® polyols, and other ethylene/polypropylene block polymers, such PEG, etc. However, as reported herein, surfactants did not generally improve release of NGF from the microspheres or stability of NGF at 37° C. When optionally present, a pharmaceutically acceptable surfactant is preferably Tween 20 or pluronic acid (F68). Amounts used are usually in the range from about 0.001% (w/v) to about 30% (w/v), more preferably from 0.005 to 0.02%. A preferred concentration for surfactant is 0.01%. Buffers include carbonate, acetate, phosphate, Tris, citrate, succinate, or histidine buffers. When present, the buffer, most advantageously, is in the range of about 2 mM to about 100 mM. Typically, the dried microsphere devices do not require buffering. Optionally, if the formulation contains a pharmaceutically acceptable salt, the salt is preferably sodium chloride, and preferably at about physiological concentrations.

Since the formulations are typically provided in dried form, a preservative is not typically needed. However, when a microsphere resuspension is used over an extended period of time, such with a pump, preservatives may be useful. Optionally, the resuspendend formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, benzalconium chloride, benzethonium chloride, and propylparaben are preferred preservatives. More preferred preservatives are 0.2–0.4% (w/v) phenol and 0.7–1.5% (w/v) benzyl alcohol. While the type of preservative and the concentration range are not critical, benzyl alcohol has been reported to enhance NGF stability in solution. A particularly preferred benzyl alcohol concentration is 0.7 to 1.2% (w/v), more preferably 0.8 to 1.0%, with a particularly preferred concentration of 0.9%.

The sustained, controlled release NGF microspheres provide several advantages over bolus injection of NGF, particularly for treatment of peripheral neuropathy. In particular, this formulation would reduce the number of injections from 3 per week to once or twice per month. In addition, the low burst and slow daily release (i.e., a low initial release) will result in lower Cmax levels and therefore reduce side effects such as local irritation or hyperalgesia. Further, the development of other indications such as nerve damage (e.g. spinal or bone fractures) would benefit from the local delivery of NGF via the microspheres. Nerve growth factor has been observed to enhance neuron survival and increase neurite outgrowth, which are effects beneficial in the treatment of peripheral neuropathy and have utility in the treatment of brain disorders such as Alzheimer's and Parkinson's disease. While a systemically administered form of NGF will not penetrate the blood brain barrier and daily injections of NGF may be necessary to treat peripheral neuropathy, the local or targeted delivery of NGF using the microsphere formulations of the invention can allow for more efficient treatment of these disorders. Localized delivery of NGF to peripheral or cerebral neurons can be achieved with biodegradable microspheres of the invention that continuously release NGF at the desired site of action. The embodiments using poly (lactic-co-glycolic acid) (PLGA) microspheres are safe and will effectively localize at or will be restricted to the site of injection in the subcutaneous space or in the brain, thus allowing for a continuous local supply of NGF to be delivered to the neurons.

The following examples are offered by way of illustration and not by way of limitation. The disclosures of all citations in the specification are expressly incorporated herein by reference.

EXAMPLES

Example I

In the development of a long acting formulation for recombinant human NGF the use of a biodegradable polymeric matrix for sustained release of NGF was investigated. The polymer used for this application was a copolymer of lactic and glycolic acids, referred to as poly(lactic/glycolic acid) or PLGA. To incorporate NGF into this polymer, the PLGA must be dissolved in a water immiscible solvent. A commonly used solvent for dissolution of PLGA has been methylene chloride which provides both water immiscibility and PLGA solubility. However, ethyl acetate is preferred. In general, for production of NGF-PLGA microspheres, the NGF was mixed in aqueous, buffered solution, with optionally present polyol stabilizers and/or a surfactant, and freeze dried. To the freeze dried NGF powder was optionally added a release modifier, such as zinc carbonate. The NGF powder was then added to a solution of ethyl acetate containing PLGA. In initial studies, the polypeptide was added in the form of a milled lyophilized powder. After polypeptide addition, the ethyl acetate solution was then briefly homogenized. In one method the solution was added to an emulsification bath, which resulted in the extraction of methylene chloride with the concomitant formation of PLGA microspheres containing NGF. In a preferred method the solution is atomized and the atomized droplets frozen. The ethyl acetate is extracted from the microspheres and the microspheres are then dried to remove traces of extraction solvent. Sieving can be used to size the microspheres. The polypeptide released from these microspheres was then studied to determine the integrity of released NGF from the microspheres. Assessment of released NGF was performed by analytical size exclusion chromatography (SEC-HPLC) as well as other techniques.

Materials

Recombinant human nerve growth factor (NGF) was produced in Chinese hamster ovary cells and purified by reversed-phase (RP-HPLC) and ion-exchange chromatography (IEC) as described previously (Schmelzer et al. (*J. Neurochem.* 59:1675–1683 (1992)). HPLC grade acetonitrile, and TFA were used for RP-HPLC. All other chemicals were USP grade. Sterile type I, clear glass, 2 cc vials were purchased from Wheaton and used with siliconized, Teflon-coated, butyl rubber stoppers.

Analytical Methods

UV Analysis. rhNGF concentration was determined by scanning from 240 to 360 nm using an HP 8452A UV-V is spectrophotometer. Formulation buffer was used as a reference to blank the instrument, and the protein concentration in mg/mL was calculated from (A278–320)/1.5, where 1.5 is the extinction coefficient of rhNGF in mL/(mg.cm).

BCA (bicinchoninic assay) using rhNGF standards was performed to determine NGF protein concentration of NGF released from the microspheres in vitro.

HPLC Analysis:

Size-Exclusion Chromatography. Size-exclusion HPLC was employed to detect and quantitate aggregate formation in the rhNGF formulations. Using this technique, rhNGF elutes as dimer (main peak) at a retention time of 8.6 minutes. The appearance of leading shoulder on the dimer main peak indicates the presence of aggregate of higher molecular weight. Size exclusion HPLC ("SEC-HPLC") was carried out using a Perkin Elmer Series 410 Bio LC Pump with a Perkin Elmer LC 90 Spectrophotometric UV Detector and a Tosohas TSK 2000 SWXL, 5 μm (7.8×300 mm) column. This SEC column was run at 0.5 m/min using a 0.2 M potassium phosphate, 0.45 M potassium chloride mobile phase, at pH 7.0. For SEC UV detection was at 280 nm; for RP-HPLC and IEC, at 214 nm.

ELISA. This assay has a range of 0.39–6.25 ng/mL. Each rhNGF sample was diluted in assay diluent to two target concentrations of 5 and 2.5 ng/mL, and each dilution was assayed in triplicate. The protein concentration in mg/mL was normalized to a −70° C. internal reference standard which was submitted for the same assay.

Radioreceptor Assay (RRA). This assay measures the ability of unlabeled rhNGF to compete with 125I-rhNGF for receptor binding on PC-12 cells. This assay has a range of 3–80 ng/mL. Each rhNGF sample was diluted in assay diluent to two target concentrations of 25 and 12.5 ng/mL, and each dilution was analyzed in duplicate. The protein concentration in mg/mL was normalized to a −70° C. internal reference standard which was submitted for the same assay.

PC-12 Cell Survival Bioassay. This assay determines the ability of rhNGF to bind to its receptors and generate intracellular signals that result in the survival of PC-12 cells under serum-free culture conditions and has a range of 0.24–30 ng/mL. The active protein concentration in mg/mL was normalized to a −70° C. internal reference standard which was submitted for the same assay.

Neurite Outgrowth Assay. The biological activity of NGF was determined using the PC12 assay developed by Greene (A quantitative bioassay for nerve growth factor activity employing a clonal pheochromocytoma cell line. *Brain Res.* 133:350–353 (1977)) and modified as described by Schmelzer et al. (*J. Neurochem.* 59:1675–1683 (1992)).

SDS-PAGE. Samples were diluted into Novex tricine SDS sample buffer and incubated for 1 hour at 50° C. Non-reduced SDS-PAGE was run on Novex tricine gels containing 10% acrylamide followed by Coomassie Blue staining. Molecular weights were estimated using Bio-Rad low molecular weight markers. Using non-reduced SDS-PAGE the monomer is at 13.5 kDa and dimer band at approximately 26 kD.

Stability of NGF at 37° C. was assessed in part by the extent of aggregation of NGF. The dimer/monomer equilibrium constant for murine NGF is smaller than 10–13 M at pH 4–7 (Bothwell et al. *J. Biol. Chem.* 252:8532–8536 (1977); Timm, et al., *Biochem.* 33:4667–4676 (1994); Moore et al., *Neurobiol.* 5:369–381 (1975); Timm et al., *Prot. Sci.* 1:236–244 (1992)). NGF, therefore, assayed primarily as a dimer in the neutral pH SEC. A small amount of aggregated NGF can be identified as tetramer based on molecular weight standards. A leading shoulder on this peak indicates larger aggregates.

In vitro release of NGF from the microspheres was measured by incubation in release buffer: 10 mM sodium acetate, 136 mM NaCl, 0.02% polysorbate 20, 0.02% sodium azide, pH 5.5. The "initial release" period was defined as one hour.

Methods

The NGF protein was observed to have the greatest physicochemical stability at pH 5.5 and was therefore formulated in 5 mM histidine, pH 5.5 (De Young, et al., *Biophys. J.* 66:A401 (1994)). Various excipients were added to this formulation buffer and then the formulations were treated with ethyl acetate as described previously (Cleland, J. L. & Jones, A. J. S. *Pharm. Res.* 13:1464–1475 (1996)). The most stable of the tested formulations was spray freeze dried by pumping the solution through an ultrasonic nozzle into liquid nitrogen and lyophilizing the frozen droplets. See FIG. 1.

The final protein powder was homogenized in a solution of 50:50 lactide/glycolide PLGA (0.2 dL/g viscosity, having hydrophilic end groups, Boehringer Ingelheim, RG502H) in ethyl acetate. The effect of zinc on the release of rhNGF was analyzed by adding different amounts of solid zinc carbonate (<5 μm particles) to the polymer-organic solvent solution. The suspension was pumped through an ultrasonic nozzle into a vessel containing liquid nitrogen and frozen ethanol (Johnson et al. *Nature Medicine*, 2:795–799 (1996)). After warming to −70° C., the ethanol extracted the ethyl acetate from the microspheres over 2–3 days. The microspheres were then filtered to remove the ethanol and dried.

Analysis of the microspheres was performed in vitro by incubation in 10 mM sodium acetate, 136 mM sodium chloride, pH 5.5 or 10 mM HEPES, 100 mM sodium chloride, pH 7.4 with 0.02% polysorbate 20 and 0.02% sodium azide in both buffers. Release studies were performed as described previously (Cleland et al., *Pharm. Res.* 13:1464–1475 (1996)). The loading of rhNGF in the PLGA microspheres was determined by dissolution in 1 N NaOH and absorptivity at 284 nm (E=1.545 (mg/mL)-1 cm-1).

Results

To assure release of intact native rhNGF, trehalose, sucrose, mannitol, polyethylene glycol (PEG, 3350 Da), and pluronic F68 (PF68) were screened for their ability to stabilize rhNGF in ethyl acetate. The results of the stability tests are presented in FIGS. 2 and 3. The most stable formulation consisted of 5 mg/mL rhNGF and 5 mg/mL trehalose. This formulation was used with and without surfactant that may be required to prevent aggregation of the rhNGF during incubation at physiological conditions. PLGA microspheres were produced with the stable rhNGF formulations and different amounts of zinc carbonate as shown in Table 1.

TABLE 1

| rhNGF PLGA microspheres[a] | | | |
|---|---|---|---|
| Loading (w/w) | Surfactant | Zn (w/w) | Release[b] |
| 11.1 | None | None | 14.8 |
| 11.4 | None | 3.0 | 1.5 |
| 10.0 | None | 6.0 | 1.0 |
| 10.8 | 0.01% PEG | None | 8.9 |
| 11.4 | 0.01% PEG | 3.0 | 0.4 |
| 9.4 | 0.01% PF68 | 6.0 | 1.6 |

[a]Microspheres prepared with same process. Surfactant were added to the liquid protein formulation prior to spray freeze drying. Zinc carbonate (Zn) was added as a solid to the polymer solution.
[b]Initial release of rhNGF from the PLGA microspheres.

Addition of solid zinc carbonate greatly reduced the initial release (1 hr incubation) from the microspheres. This result may be caused by the binding of rhNGF to zinc (one zinc binding site per monomer) to form a reversible noncovalent aggregate (Holland et al., *J. Mol. Biol.* 239, 385–400 (1994)). Similar results were reported for the use of zinc carbonate to modulate the release of another zinc binding protein, human growth hormone. The rhNGF PLGA formulations containing zinc also had a slower overall rate of release as shown in FIG. 4. These microspheres released all of the encapsulated rhNGF within 14 days while microspheres without zinc released most of the rhNGF within 7 days. The release rate was not affected by the addition of surfactant to the protein formulation (FIG. 5).

Another important consideration was the stability of the rhNGF during release from the microspheres at 37° C. rhNGF released initially from the microspheres was slightly aggregated (94% native dimer) and the addition of the surfactant to the protein formulation did not significantly increase the amount of native dimer (see FIG. 6). The ability of the rhNGF to bind its receptor was also reduced. A further reduction in the fraction of native dimer released from the microspheres was observed after incubation for 7–10 days at 37° C. suggesting that the rhNGF was not stable under these conditions, even in a low pH release buffer (pH 5.5).

The PLGA microsphere formulations in this example provided a continuous release of rhNGF over 7 to 14 days.

The rate of release was modulated by the addition of solid zinc to the polymer phase. The zinc and rhNGF may form a stable complex that slowly dissociates from the PLGA microspheres. While the trehalose formulation with and without surfactant appeared to provide good stability in screening studies, it did not result in the release of native rhNGF for the duration of the release. While these results indicate a controlled release of NGF in microspheres, improvements in formulation to maintain NGF stability to assure the release of native dimer throughout the duration of release are presented herein.

Example II

Because the in vitro release studies in Example I showed that encapsulated rhNGF degraded via aggregation (at 37° C., rhNGF released from the microspheres was aggregated—85% native dimer—after incubation for 10 days, as determined by SEC), a novel preformulation was employed. In this novel preformulation, a metal ion was complexed to the rhNGF prior to admixture with the biodegradable polymer. Surprisingly, a significant improvement in the stability (integrity) of released NGF from the microspheres was observed.

Zinc acetate was added to a solution of rhNGF formulated in 4 mM $NaHCO_3$, at pH 7.4. Increasing the zinc acetate concentration decreased the amount of aggregate formation, as determined by SEC (FIG. 7). FIG. 7 depicts the integrity as percent monomer of the zinc-containing NGF solutions before and after freeze-drying prior to encapsulation. Zinc-containing rhNGF solutions that had been incubated as liquid at 5 and 37° C. were opalescent after 4 weeks of storage. In contrast, under the same storage conditions, the lyophilized samples formed a precipitate after reconstitution. To determine the minimal amount of zinc required for the formation of rhNGF-Zn complex, the precipitate of the lyophilized rhNGF samples with various molar ratios of protein to zinc was removed by centrifugation, and the protein concentration (without zinc complexation) remained in the supernatant was determined by UV. As shown in FIG. 8, more than 80% of the lyophilized rhNGF complexed with zinc acetate at molar ratios of 1:6 and 1:8 (rhNGF: zinc acetate) at 5° C. Thus, another indication of the integrity, as depicted in FIG. 8, is the amount of NGF complexed with zinc and remaining in solution before and after freeze-drying prior to encapsulation. As can be seen, after four weeks at 37° C., the metal ion added to the NGF solution prior to encapsulation aids in maintaining the integrity of the NGF dimer. These findings confirm that the preformulation in aqueous solution of NGF with a metal ion that binds NGF, prior to drying the solution and admixing with additional release modifiers or biopolymer, provides a means to improve and assure the stability of encapsulated rhNGF during microspheres fabrication process and during subsequent release in vitro. Thus, the present example shows that rhNGF can be stabilized by complexing the protein with zinc acetate in solution prior to encapsulation.

This preformulation was further characterized. Purified rhNGF that was produced in CHO cells was formulated as liquid at 5.5 mg/mL in 4 mM sodium bicarbonate, pH 7.4. Zinc acetate was added to the rhNGF solution at a molar ratio of 1:10 (rhNGF: zinc acetate). Throughout all examples, by one mole of rhNGF is meant one mole of the active dimer form. The zinc-containing rhNGF solution was spray freeze dried in liquid nitrogen and lyophilized to produce solid rhNGF for microencapsulation. This solid protein (10% w/w) was then homogenized with PLGA (RG502H, 50:50, unblocked, 12 kDa) that was dissolved in ethyl acetate to form a suspension. Zinc carbonate (6% w/w) was also added to the polymer solution and homogenized before the solid rhNGF was added. After homogenization, the protein-polymer suspension was spray freeze dried in liquid nitrogen and cold ethanol to produce rhNGF/PLGA microspheres.

In vitro release studies were performed using a centrifugal ultrafiltration device. Ten mg microspheres was added to the removable reservoir of the device and mixed with 300 FL of release buffer (phosphate buffered saline, pH 7.4). The device was incubated at 37EC. After released protein was sampled by centrifugation, the device-was replenished with release buffer. Protein concentration of released rhNGF was determined using bicinchoninic acid (BCA) measurement. Native size exclusion chromatography (SEC) was employed to determine integrity (percent not aggregated) of the reconstituted solid and released rhNGF.

The effect of zinc on stabilizing rhNGF was investigated by comparing the release profile and integrity of released rhNGF with the micropsheres prepared without the addition of zinc acetate in the protein formulation (5 mM histidine buffer, pH 5.0) as described in Example 1. In this particular example, a preferred molar ratio of 1:10 (rhNGF: zinc acetate) was chosen, which was observed to significantly reduce aggregation of the protein at this minimum ratio when the suspension was stored at 37° C. The addition of zinc acetate to the protein formulation did not affect the overall in vitro release profile as shown in FIG. 9. Both rhNGF/PLGA formulations, with and without zinc acetate in the protein phase, had a low initial burst of about 1%. The microspheres prepared from both formulations released all the encapsulated rhNGF within 14 days.

The effect of zinc acetate on stability of the rhNGF during release from the microspheres at 37° C. was also studied. As presented in FIG. 10, the released protein of the rhNGF/PLGA formulation containing zinc acetate had 93% native dimer after incubation at 37° C. for 10 days while the formulation without zinc acetate released protein with 85% native dimer. In fact, the rhNGF released initially from the PLGA formulation without zinc acetate was slightly aggregated (94% native dimer).

The results in this Example indicate that the addition of zinc acetate to the protein formulation greatly reduced the aggregation of the rhNGF and thus stabilized the protein during encapsulation and subsequent release from the microspheres. The stabilization may be caused by the complexing of rhNGF with zinc to form stable aggregates. Although solid zinc (6% w/w zinc carbonate) was also added in the polymer phase during encapsulation to reduce the initial burst of the encapsulated rhNGF, it did not help to stabilize the protein. In addition, Zn:rhNGF complex only forms at high pH (pH 7.4) and dissociates at low pH (pH 5.5). At 37° C., rhNGF in the bicarbonate formulation (pH 7.4) containing zinc acetate was as stable as the protein in the control liquid formulation without zinc acetate (5 mM histidine, pH 5.5) as shown in FIG. 10. Previous studies (data not shown) showed that rhNGF was not stable at pH 7.4 without zinc. This suggests that the rhNGF may be stabilized by forming a zinc (metal ion) complex, in the absence of which rhNGF may be degraded rapidly at such a high pH. Consequently, as taught herein, rhNGF formulated in 4 mM sodium bicarbonate at pH 7.4 with the addition of zinc acetate improved the stability of the protein during microencapsulation and release at 37° C. (physiological temperature). The rhNGF in this formulation was stabilized by the formation of a zinc complex.

Typically, the NGF-metal solution is spray freeze dried, preferably by atomization of the solution into liquid nitrogen, placing the frozen droplets at a temperature less than or equal to about 70° C., followed by removal of the nitrogen, and lyophilization of the frozen droplets or crystals to achieve an NGF-metal salt powder of very fine particle size, typically less than about 5 microns. The NGF-zinc powder is processed into a controlled release microsphere as taught herein, preferably as discussed in Example 1. The amount of NGF loaded into the microspheres is typically 10% (w/w).

For an injectable, the microspheres are sieved, preferably to a 20 to 90 micron size. The bulk, sieved microspheres are vialed in an amount suitable for resuspension and injection. For subcutaneous injection the microspheres are resuspended in 5% dextran −70 in saline solution (9% NaCl) with optional 0.01% Tween 20. Alternatively, the rhNGF/zinc/PLGA microspheres are resuspended and are injected into an implanted Ommaya reservoir (or the like) in the brain for the continuous release of rhNGF for 3–4 weeks.

What is claimed is:

1. A polymeric microsphere device having a diameter of less than about 1000 microns for sustained controlled release of NGF and another neurotrophic factor selected from NT-3, NT-4/5, BDNF, and combinations thereof, comprising a biocompatible polymeric microsphere containing about 0.1% to about 50% NGF by weight complexed with an NGF-stabilizing metal that binds NGF, and another neurotrophic factor selected from NT-3, NT-4/5, BDNF, and combinations thereof, which device is capable of releasing NGF over a period of time in excess of about one day.

2. The polymeric microsphere device of claim 1, wherein the microspheres have a particle size of between about 0.1 microns and about 300 microns.

3. The polymeric microsphere device of claim 1, wherein the microspheres have a particle size of between about 1 micron and about 150 microns.

4. The polymeric microsphere device of claim 1, wherein the microspheres have a particle size of between about 2 microns and about 100 microns.

5. The polymeric microsphere device of claim 1, wherein the microspheres have a particle size of between about 20 microns and about 90 microns.

6. A method of making a microsphere device for controlled sustained release of neurotrophic factors, comprising:

mixing NGF in solution with an NGF-stabilizing salt of a metal that binds NGF, wherein the molar ratio of NGF to the metal is from about 1 to 4 to about 1 to 50, and microencapsulating the NGF-metal mixture with another neurotrophic factor selected from NT-3, NT-4/5, BDNF, and combinations thereof to form a biocompatible polymeric microsphere capable of controlled sustained release of NGF containing about 0.1% to about 50% NGF by weight complexed with an NGF-stabilizing metal that binds NGF, and another neurotrophic factor selected from NT-3, NT-4/5, BDNF, and combinations thereof.

7. The method of claim 6, wherein the microspheres have a particle size of between about 1 micron to about 1000 microns.

8. The method of claim 6, wherein the microspheres have a particle size of between about 0.1 microns and about 300 microns.

9. The method of claim 6, wherein the microspheres have a particle size of between about 1 micron and about 150 microns.

10. The method of claim 6, wherein the microspheres have a particle size of between about 2 microns and about 100 microns.

11. The method of claim 6, wherein the microspheres have a particle size of between about 20 microns and about 90 microns.

* * * * *